US010025207B2

(12) United States Patent
Rangelow

(10) Patent No.: US 10,025,207 B2
(45) Date of Patent: Jul. 17, 2018

(54) METHOD OF ALIGNING A FIRST ARTICLE RELATIVE TO A SECOND ARTICLE

(75) Inventor: Ivo Rangelow, Baunatal (DE)

(73) Assignee: Universität Kassel, Kassel (DE)

( * ) Notice: Subject to any disclaimer, the term of this patent is extended or adjusted under 35 U.S.C. 154(b) by 0 days.

(21) Appl. No.: 13/102,469

(22) Filed: May 6, 2011

(65) Prior Publication Data

US 2011/0219635 A1 Sep. 15, 2011

Related U.S. Application Data

(62) Division of application No. 11/572,046, filed as application No. PCT/EP2005/007677 on Jul. 14, 2005, now Pat. No. 7,946,029.

(30) Foreign Application Priority Data

Jul. 14, 2004 (EP) ..................................... 04016571

(51) Int. Cl.
*G03F 9/00* (2006.01)
*G01Q 60/16* (2010.01)
(Continued)

(52) U.S. Cl.
CPC ........... *G03F 9/7061* (2013.01); *G01Q 20/00* (2013.01); *G01Q 20/04* (2013.01); *G01Q 60/16* (2013.01);
(Continued)

(58) Field of Classification Search
CPC ........ G01Q 20/00; G01Q 20/04; G01Q 60/16; G01Q 70/06; G01Q 80/00; G01Q 60/34; B82Y 10/00; G03F 9/7061; G03F 9/7038; G03F 9/7042; Y10T 29/42; Y10T 29/49005; Y10T 29/49131; Y10T 29/49133; Y10T 29/49774;
(Continued)

(56) References Cited

U.S. PATENT DOCUMENTS 4,437,235 A 3/1984 McIver
5,166,520 A 11/1992 Prater et al.
(Continued)

FOREIGN PATENT DOCUMENTS

DE 10303040 A1 10/2003
EP 1351256 A2 10/2003
(Continued)

OTHER PUBLICATIONS

Gotszalk T. et al., "AFM With Piezoresistive Wheatstone Bridge Cantilever-Noise Performances and Applications in Contact and Noncontact Mode", Proceedings of the SPIE, SPIE, Bellingham, VA, US. vol. 2780, Sep. 11, 1995.
(Continued)

*Primary Examiner* — A. Dexter Tugbang
(74) *Attorney, Agent, or Firm* — Dinsmore & Shohl LLP

(57) ABSTRACT

A method for aligning a first article relative to a second article. The second article is provided with at least one flexible structure fixed to the second article at one point while the first article includes at least one surface relief marking. A detector measures the interaction between the flexible structure and surface relief marking and generates detector signals relative to that interaction to achieve alignment between the first and second articles.

12 Claims, 14 Drawing Sheets

(51) Int. Cl.
*G01Q 20/00* (2010.01)
*G01Q 70/06* (2010.01)
*G01Q 20/04* (2010.01)
*G01Q 60/34* (2010.01)
*G01N 23/046* (2018.01)
*B29C 64/135* (2017.01)
*B82Y 10/00* (2011.01)
*G01Q 80/00* (2010.01)

(52) U.S. Cl.
CPC .......... *G01Q 70/06* (2013.01); *G03F 9/7038* (2013.01); *G03F 9/7042* (2013.01); *B29C 64/135* (2017.08); *B82Y 10/00* (2013.01); *G01N 23/046* (2013.01); *G01Q 60/34* (2013.01); *G01Q 80/00* (2013.01); *Y10T 29/42* (2015.01); *Y10T 29/49005* (2015.01); *Y10T 29/49131* (2015.01); *Y10T 29/49133* (2015.01); *Y10T 29/49744* (2015.01); *Y10T 29/49778* (2015.01); *Y10T 29/53261* (2015.01); *Y10T 29/53265* (2015.01)

(58) Field of Classification Search
CPC ......... Y10T 29/49778; Y10T 29/53261; Y10T 29/53265; B29C 67/0066; B29C 64/135; G01N 23/046
USPC .............. 29/25.35, 594, 833, 834, 759, 760, 29/407.07, 407.09; 250/306, 307, 309, 250/311
See application file for complete search history.

(56) References Cited

U.S. PATENT DOCUMENTS

| | | | |
|---|---|---|---|
| 5,266,801 A * | 11/1993 | El Ings et al. | |
| 5,317,141 A | 5/1994 | Thomas | |
| 5,444,244 A | 8/1995 | Kirk et al. | |
| 5,883,705 A | 3/1999 | Minne et al. | |
| 6,066,774 A | 7/2000 | Ho et al. | |
| 6,441,371 B1 * | 8/2002 | Ahn et al. | 60/34 |
| 6,519,838 B1 | 2/2003 | Okuda et al. | |
| 6,583,411 B1 * | 6/2003 | Altmann et al. | |
| 6,734,425 B2 | 5/2004 | Hantschel et al. | |
| 6,955,767 B2 | 10/2005 | Chen | |
| 7,353,594 B2 | 4/2008 | Yoshida et al. | |
| 2001/0028033 A1 * | 10/2001 | Shimizu | G01N 23/046 250/309 |
| 2001/0038072 A1 | 11/2001 | Aumond et al. | |
| 2002/0170880 A1 | 11/2002 | Chen | |
| 2003/0003179 A1 * | 1/2003 | Farnworth | B29C 67/0066 425/174.4 |

FOREIGN PATENT DOCUMENTS

| | | | |
|---|---|---|---|
| JP | 03185812 A * | 8/1991 | |
| JP | 5303781 A | 11/1993 | |
| JP | 2001033373 A * | 2/2001 | |
| WO | WO-02/077716 A2 | 10/2002 | |

OTHER PUBLICATIONS

Gotszalk T. et al., "Fabrication of Multipurpose Piezoresistive Wheatstone Bridge Cantilevers With Conductive Microtips for Electrostatic and Scanning Capacitance Microscopy", pp. 3948-3953, J. Vac. Sci. Technol. B 16(6), Nov. 12, 1998.
Baselt, D., "Atomic Force Microscopy", California Institute of Technology, Copyright © 1993.
Pang, S. et al., "Micromachining and Microfabrication Process Technology II", SPIE vol. 2879, pp. 56-64, Oct. 14-15, 1996.
Pedrak, et al. "Micromachined Atomic Force Microscopy Sensor With Integrated Piezoresistive Sensor and Thermal Bimorph Actuator for High-Speed Tapping-Mode Atomic Force Microscopy Phase-Imaging in Higher Eigenmodes", J. Vac. Sci. Technol. B 21(6), Nov. 12, 2003, pp. 3102-3107.
Mancini, D. et al., Analysis of Critical Dimension Uniformity for Step and Flash Imprint Lithography, Physical Sciences Research Laboratories, Motorola Labs, Emerging Lithographic Technologies VII. Proceedings of the SPIE, vol. 5037, pp. 187-196, Jun. 2003.
Solin, S., "Nanoscopic Magnetic Field Sensor Based on Extraordinary Magnetoresistance*", J. Vac. Sci. Technol, B 21 (6), Nov. 12, 2003, pp. 3002-3006.
Xia et al., Soft Lithography, Angew. Chem., Int. Ed. Engl. 37, 550 (1998), pp. 153-184.
Colburn, M. et al., "Step and Flash Imprint Lithography: A New Approach to High-Resolution Patterning", Proc. SPIE 379 (1999).
Chou, S., et al., "Nanoimprint Lithography", J. Vac. Sci Technol. B 14(6), Nov. 12, 1996, pp. 4129-4133.
Resnick, D.J., et al., "High Resolution Templates for Step and Flash Imprint Lithography", JM3 1(3), Oct. 2002, pp. 284-289.

* cited by examiner

METHOD OF ALIGNING A FIRST ARTICLE RELATIVE TO A SECOND ARTICLE

CROSS-REFERENCE TO RELATED APPLICATIONS

This application is a divisional of U.S. patent application Ser. No. 11/572,046 filed Mar. 7, 2007, now U.S. Pat. No. 7,946,029, which is the U.S. national phase of PCT/EP2005/007677 filed Jul. 14, 2005, which claims priority of European Patent Application No. 04016571.4 filed Jul. 14, 2004.

FIELD OF THE INVENTION

The present invention relates to a method of aligning a first article relative to a second article and to an apparatus for aligning a first article relative to a second article and has particular reference to a method and to an apparatus for the high precision alignment of two articles, e.g. to a positional accuracy better than ten nanometers and preferably better than one nanometer.

BACKGROUND OF THE INVENTION

Currently alignment techniques are known, e.g. in the field of semiconductor manufacture, where an alignment with a positional accuracy of about 100 nm can be achieved with optical techniques. However, it is very difficult to achieve an alignment accuracy significantly better than 10 nm because of the diffraction limit which applies to the resolution of optical alignment techniques.

There are some semiconductor manufacturing processes involving nano-structures which would benefit from an alignment accuracy of better than 10 nm and preferably of around 1 nm which cannot currently be achieved, or can only be achieved with significant technical complexity. One such application is the manufacture of semiconductor circuits using templates and curable resins to define the circuit patterns which are to be realized. Such manufacturing processes are summarized below.

There are also other technical fields in which a high alignment accuracy is either currently desirable or which could benefit from such high alignment accuracies, if suitable methods and apparatus for achieving alignment accuracies of tens of nm or better were available in a production environment. For example, there is increasing interest in nano-electronics, molecular electronics, single electron devices, or microfluidic devices which could be made significantly smaller if higher alignment accuracies could be achieved.

Similarly applications for high precision alignment apparatus and methods are conceivable in the biological or chemical fields. For example one could conceive a holder for biological or chemical use having an array of regularly (or irregularly) positioned recesses on a nanometer scale, each containing a sample or a reagent which has to be brought together with high positional accuracy with a carrier having reagents or samples positioned on a complementary array of projections which have to engage in the aforementioned recesses.

In nanoimprint lithography in which a negative three dimensional pattern provided on a template, for example of fused silica, is transferred to a thin layer of silicon containing monomer on a semiconductor or insulating substrate which is subsequently polymerized by UV illumination to form a hard positive pattern of the cured polymer on the surface of the substrate. In this technique the cured polymer is subsequently etched to remove a residual layer of polymer between raised features of the pattern and to reach the substrate material at these positions. Thereafter, the substrate may be etched further to produce depressions in the substrate material, and increase the aspect ratio of the raised features relative to the depressions, i.e. the depth of the depressions relative to the raised features. Then the residual polymer can be stripped from the substrate and one or more layers of semiconducting or insulating or conducting material deposited on the substrate. Following this, and appropriate polishing of the surface of the substrate, an organic planarization layer is deposited on the substrate and the process is then repeated using a different template and a new layer of UV-curable imprint solution. This process is then repeated for further templates, for example frequently using twenty or thirty different templates to produce the finished semiconductor circuit. This process, known e.g. under the name S-FIL™, a registered trade mark of Molecular Imprints Inc., is discussed, together with other lithographic processes, in more detail in an appendix to the present application.

The templates used are for example available to order from firms such as DuPont Photomasks and Photronics, who currently take orders for S-FIL templates down to 100 nm feature sizes. Only the template fabrication process, typically accomplished with an e-beam writer, limits the resolution of the features. Features as small as 20 nm have been made to date that exceed the present requirements specified in the International Technology Roadmap Semiconductors (ITRS). With this background in mind it will be appreciated that, although there is generally no critical alignment problem with applying the first imprint to a substrate using a first template, any subsequent template requires critical alignment with the pattern determined by the first and succeeding templates if the semiconductor circuit is to have any chance of operating as desired. The present invention provides such a tool.

In known processes of manufacturing semiconductors surface relief markings are regularly applied to semiconductor wafers to enable alignment of a series of masks or imprint templates with the wafer. They are however recognized and used for alignment by optical systems which, as explained above, have a diffraction limited resolution limit of about 100 nm. The same surface relief markings can be used for the purposes of the present invention. However, it can be preferable to make them smaller and for to position them with a smaller pitch. The surface relief markings can also be made with special topographies which enable them and/or their position to be detected more accurately and for reliably.

One proposal for achieving high accuracies in the alignment of a patterned mold (a first article) with a substrate (a second article) suitable for the manufacture of a semiconductor structure by an imprint process is described in the published international patent application WO 02/077716. That document describes a lithographic method which comprises aligning a patterned mold with respect to an alignment mark disposed on the substrate. The detection process is based upon interaction of a scanning probe with the alignment mark. The alignment mark can be formed by the edges of relief features provided on the substrate outside of the area to be patterned.

In the system described in WO 02/077716 an optical alignment system is first used to approximately align the patterned mold with the substrate and the precise alignment of the patterned mold with the substrate is then effected by a scanning probe alignment system either realized as a scanning tunnel microscope scanning assembly, in which the positions of the probes and thus of the patterned mold are controlled based on tunneling current information, or implemented as an atomic force microscope scanning assembly, in which the positions of probes are controlled based upon a force (e.g. an atomic force, an electrostatic force or a magnetic force) that is generated between the probes and one or more alignment marks carried on the substrate.

More specifically the scanning system is configured to move a scanning head, which carries the patterned mold and the probes, precisely in a plane, the x-y plane, that is parallel to the support surface of a stationary block carrying the substrate. The scanning system is also configured to move the scanning head precisely in the z-direction which is orthogonal to the support surface of the stationary block. It is stated that in one embodiment the scanning head may be moved vertically by a z-axis scan actuator and horizontally by a separate x-y axis scan actuator.

The actuators can be implemented as planar electrostatic actuators and can both be carried on the scanning head. After scanning the alignment mark in the x-y plane using the x-y scan actuator the precise position of the alignment mark relative to the patterned mold can be determined and the x-y actuators used to move the patterned mold into the desired alignment with the alignment marks and thus the substrate for the patterning process. The z-actuator can then be used to move the patterned mold vertically to impress the pattern thereon into a moldable film provided on the substrate. It is also stated that the probes can be retracted after alignment prior to the movement in the z-direction. However, it is not explained how this can be done.

The problem with the scanning system described in WO 02/077716 is that the detection of the alignment marks through scanning movement of the probes takes a relatively long time. This means that the manufacturing process for the semiconductor structure, which can involve the use of many imprint steps, with processing steps following each imprint step thus requiring repeated realignment, takes a relatively long time, which is undesirable. It should be appreciated that this applies irrespective of whether the scanning system is realized as a scanning tunnel microscope or is based on an atomic force microscope scanning assembly in which the positions of the probes are controlled based upon a force, such as an atomic force, an electrostatic force or a magnetic force. As those skilled in the art of atomic force microscopes will know these are all time-consuming non-contact measurement techniques. U.S. Pat. No. 5,317,141 describes a similar system to WO 02/077716. The principal difference is that the US patent is concerned with the alignment of a mask for X-ray lithography with a wafer, for subsequent patterning of the wafer using x-ray beams directed through the X-ray mask. Again a scanning probe microscope is used, e.g. in the form of an atomic force microscope which functions by scanning a fine-tipped probe over the surface of an alignment mark on the wafer or substrate. More specifically, a voltage difference is applied between the probe and the alignment mark and the tunneling current which results when the probe is a small distance from the surface is detected. For this system the alignment mark must have a conductive surface.

This is again a non-contact measurement. The detection of the tunneling current during scanning of the probe over the alignment mark is effected by a piezoelectric block carrying the probe. Control voltages can be applied to electrodes on the piezoelectric block to first energize it to move the probe in the z-direction to detect a tunneling current as the probe approaches the surface of the alignment mark. Thereafter further control voltages can be applied to appropriately positioned electrodes on the piezoelectric block to produce scanning movement of the probe in the x- and y-directions. The variation in the tunneling current and thus the topology of the alignment mark can then be determined during the scanning movements. This allows the position of the sensing head relative to the alignment mark to be determined with high accuracy. Because of the restriction involving the need for the alignment mark to have a conductive surface the US patent also discloses a second system in which a contact arm touches the surface of the alignment mark and the sensing tip is carried by the piezoelectric block at a small distance above the arm. The arm is electrically conductive so that the tunneling current can be measured between the arm and the tip of the probe which is spaced from the arm. The distance between the arm and the tip of the probe varies as the probe and arm are scanned over the surface of the alignment mark. Again the scanning of the alignment mark is relatively slow.

For the sake of completeness reference should also be made to two further documents which refer generally to atomic force microscopy. The first is DE-A-103 03 040 which describes a non-contact mode detector incorporated in a cantilever. This non-contact mode detector is also described, together with other non-contact detectors, in the paper: Micromachined atomic force microscopy sensor with integrated piezoresistive sensor and thermal bimorph actuator for high speed non-contact mode atomic force microscopy phase imaging in higher eigenmodes by R. Pedrak, Tzv. Ivanov, K. Ivanova, T Gotszalk, N. Abedinov, I. W. Rangelow, K. Edinger, E. Tomerov, T. Schenkel and P. Hudek in J. Vac. Sci. Technol. B 21(6) November/December 2003 pages 3102 to 3107. More specifically the above referenced article describes microprobes for non-contact scanning force microscopy, more specifically tapping mode atomic force microscopy. In this arrangement a cantilever carrying a tip is excited to oscillate close to its resonance. The topography information is collected from the phase lag between vibration excitation and response of the cantilever deflection sensor.

In one embodiment described in the above referenced article the cantilever is realized as a bimorph actuator involving an aluminium layer on a silicon dioxide cantilever. The aluminium layer can be heated with an oscillating current to produce oscillatory bending deflection of the cantilever due to differential thermal expansion. In one embodiment described in the paper the cantilever is configured to include a piezoresistive detector realized in the form of a Wheatstone bridge.

The production of probes for atomic force microscopy, including a probe which utilizes a piezoresistive Wheatstone bridge is also described in the document SPIE Vol 2879/ pages 56 to 64, being a paper presented at a conference in Texas on Oct. 14-15, 1996. A piezoresistive detector incorporated in a cantilever is also described in U.S. Pat. No. 5,444,244.

SUMMARY OF THE INVENTION

It is therefore a principle object of the present invention to provide a method and an apparatus for accurately aligning a first article with a second article with a positional accuracy better than 100 nm, preferably better than 10 nm and in particular approaching 1 nm or better at a significantly higher speed than is possible in the prior art, thus speeding up production processes such as the manufacture of semiconductor substrates by imprint lithography.

In order to satisfy this object there is provided a method of aligning a first article with a second article comprising the steps of:

providing said second article with at least one flexible structure fixed relative thereto at least one point, providing a first article having at least one surface relief marking, providing a detector for measuring an interaction of the flexible structure with the surface relief marking and generating detector signals relating to said interaction, identifying with the help of the detector signals the position of the flexible structure and thus of the second article with respect to the surface relief marking and generating relative movement between the first and second articles to achieve a desired alignment between the first and second articles defined by the surface relief marking, the method being characterised in that said detector detects deflection of said flexible structure by a tip of the flexible structure, e.g. a cantilever tip, touching the surface, the detector preferably being selected from the group comprising: a reflecting surface provided on said flexible structure and an associated optical detection system for measuring said deflection at said reflecting surface, a piezoresistive structure incorporated at said flexible structure, a piezoelectric structure incorporated at said flexible structure, a capacitive detector for detecting deflection of said flexible structure, an inductive detector for detecting deflection of said flexible structure and a surface acoustic wave structure incorporated at said flexible structure.

Also according to the present invention there is provided an apparatus for aligning a first article with a second article, said first article having at least one surface relief marking and said second article having at least one flexible structure, means for positioning one of said first and second articles adjacent to the other one with provision for at least restricted relative movement between said first and second articles, a detector for detecting deflection of said at least one flexible structure due to an interaction with said at least one surface relief marking and providing detecting signals relating to said interaction, a memory containing stored information related to a topology of said surface relief marking, means for comparing said detection signals with said stored information to generate position control signals relating to a desired alignment and steering means for steering movement of at least one of said first and second articles relative to the other to achieve said desired alignment the apparatus being characterised in that said detector is adapted to detect deflection of said flexible structure by a tip of the flexible structure, e.g. a cantilever tip, touching the surface, the detector preferably being selected from the group comprising: a reflecting surface provided on said flexible structure and an associated optical detection system for measuring said deflection at said reflecting surface, a piezoresistive structure incorporated at said flexible structure, a piezoelectric structure incorporated at said flexible structure, a capacitive detector for detecting deflection of said flexible structure, an inductive detector for detecting deflection of said flexible structure and a surface acoustic wave structure incorporated at said flexible structure.

A method and an apparatus of the above kind are very advantageous. Since the tip of the flexible structure actually touches the alignment mark, or at least prominent edges of it, scanning movement to detect the alignment mark can be carried out very fast, thus significantly reducing the processing time required to detect the position of the alignment mark and thus to align the first article with the second for the imprint process. There is no need to vary the distance between the second article carrying the flexible structure and the first article once the flexible structure has touched the surface of the first article, i.e. the alignment mark provided thereon. The alignment mark is preferably provided with sharp edges which enhance the detection signals resulting from deflection of the flexible structure as it is moved across the alignment mark, which can be done relatively rapidly.

In a particularly preferred embodiment of the method and the apparatus the flexible structure is provided as a bimorph structure enabling it to be heated electrically resulting in differential expansion of two layers of the flexible structure (which may be a cantilever) and thus bending deflection which allows the tip on the flexible structure to be retracted during the imprint patterning movement so that the neither the flexible structure nor the tip is damaged during the imprint process. This retraction movement can be realized almost instantaneously following the designed alignment having been achieved so that essentially no time is lost by this operation. In principle it is only necessary to provide a single surface relief marking on the first article or substrate, i.e. a surface relief marking at one position on the first article or substrate, providing this marking has sufficient differently aligned features that it can be recognized by interaction with the flexible structure and allow precise alignment to be achieved. Generally it is however simpler to provide a plurality of surface relief markings on the first article or substrate, i.e. surface relief markings at different locations on the first article or substrate because these can be made more simply and recognized more simply. The markings could, for example, then comprise a plurality of raised bars or bar-like depressions at one point on the margin of an article or wafer and a second, like, set of surface relief markings at a different angular orientation (e.g. at 90° to the first set) at a different position on the margin of the article or wafer (e.g. displaced around an axis of the article or substrate by 90° relative to the first set).

If a plurality of surface relief markings are provided then it is generally convenient if a like plurality of flexible structures is provided on the second article, which are placed in juxtaposition to the respective surface relief markings.

The surface markings are typically surface relief markings which are integrally formed with said first article. For example, in the case of a semiconductor wafer, the surface relief markings can be formed on the wafer by electron beam writing or by any suitable lithography process.

In principle the surface relief marking can be a natural feature of said first article, e.g. surface features such as corrugations or pyramids formed by self organization of the surface or natural structures or faults. Alternatively it can be an artificial feature formed on or bonded to the first article. In similar fashion the or each flexible structure can be integrally formed with said second article or can be distinct from said second article, but physically connected thereto.

The flexible structure can be selected from the group comprising: a cantilever, a flexible bridge supported at two points and a flexible membrane supported at a plurality of points. The most convenient design is a cantilever, for example a cantilever as is used in an atomic force microscope. The detector is typically adapted to detect a deflection of said flexible structure which arises as a result of the interaction.

As mentioned, the first article can be a semiconductor wafer or an insulating substrate, or a substrate with a partially completed semiconductor structure formed thereon. It can also be a glass, metal or plastic article, a biological sample carrier or a chemical sample carrier or can take some other form. It can, for example, also be a planar or contoured surface of a three dimensional body.

The second article can be a template for nanoimprint lithography as described above or a biological sample dispenser, a chemical sample dispenser, a biological sample readout device or a chemical sample readout device or some other article.

A means will generally be provided for steering movement of said second article relative to said first article in order to achieve the requisite alignment. Thus, either the first article can be held stationary and the second article moved relative to it, or vice versa. Alternatively, the first and second articles can both be moved simultaneously.

More specifically, said steering means can be selected, without limitation, from the group comprising piezoelectric actuators, thermal actuators, electromagnetic actuators, and oscillatory actuators. With an oscillatory actuator the second article would oscillate relative to the first and the second article could be moved into contact with the first at the correct position of alignment reached at some point during the oscillatory movement, thus arresting the oscillatory movement, at least temporarily; for example, for the duration of an S-FIL imprint step.

It is not essential to provide relative movement of the second article relative to the first in order to find the correct alignment, although a relative movement of this kind will generally be provided in order to enable the flexible structure to interact with the surface relief marking. It would for example be possible to realize the flexible structure as one moveable in two distinct planes, for example in two planes orthogonal to one another. In this case the flexibility in one plane could be used to sense the distance to the surface, i.e. to find whether a step or edge in the surface relief marking is present, whereas the movement in the second plane, which would be a steered movement, caused for example by bending of a cantilever when subjected to heating, is used to traverse the surface relief marking in a direction generally parallel to the surface of the first article. Thus a cantilever as described in the above referenced article could be provided with bimorph properties on two orthogonal surfaces of the cantilever.

BRIEF DESCRIPTION OF THE DRAWINGS

The above described methods can be repeated using a third article or further articles provided with a flexible structure and cooperating with said surface relief marking provided on said first article. Further preferred embodiments of the invention are described in the claims and in the following description of preferred embodiments given with reference to the accompanying drawings in which:

DETAILED DESCRIPTION OF THE PREFERRED EMBODIMENTS

Figure 1:
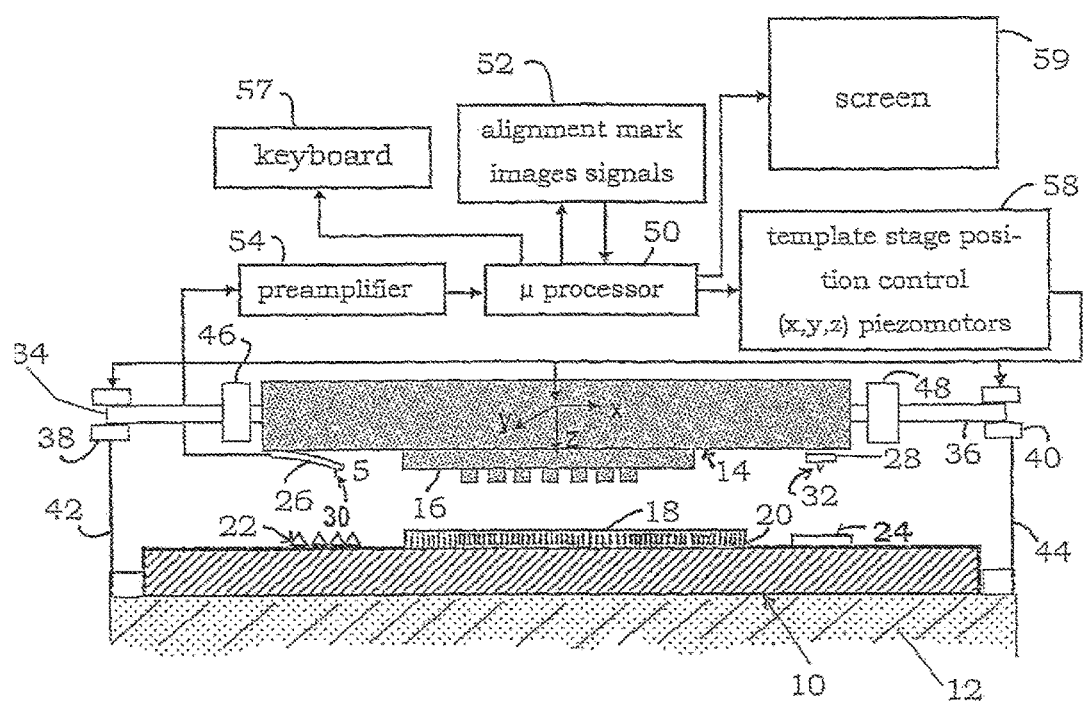
FIG. 1 shows a schematic diagram of an apparatus in accordance with the present invention.

Referring first to FIG. 1 there can be seen a first article 10, here in the form of a semiconductor wafer, which is rigidly mounted on a fixed table 12. Positioned above the first article 10 and facing it is an adjacent second article, here in the form of a silicon wafer 14 carrying a template 16 which is to be used in a nanoimprint lithography step using the S-FIL process to pattern an imprint resist layer 18 deposited on an imprint area 20 of the semiconductor wafer forming the first article 10.

In this embodiment the first article 10 has first and second surface relief markings 22 and 24. The surface relief marking 22 is illustrated as a row of triangular bars provided locally on the surface of the first article 10 and seen end on in this drawing. The second surface relief marking 24 is essentially identical to the surface relief marking 22 but is rotated through 90° relative to the marking 22 thus the bars are seen side on in the marking 24. It will be appreciated that the markings 22 and 24 have a fixed position relative to the imprint area 20 and any circuit pattern provided thereon. Accordingly, if appropriate reference marks on the second article 14, which have a fixed position relative to the template 16, are accurately aligned with the markings 22 and 24 then, assuming the template is correctly positioned with respect to the reference marks, the template is accurately aligned with the imprint area 20 and any circuit pattern provided thereon.

In the present embodiment the reference marks on the second article 14 take the form of first and second flexible structures 26, 28 which are each realized as a cantilever beam. The cantilever beam 26 forming the first flexible structure is seen side on in FIG. 1 and carries a fine tip 30 which is formed in the manner of a fine tip typically used in atomic force microscopy (i.e. a tip which is preferably just one atom wide at the point) and is able to touch and scan across the surface relief marking 22 in the x-direction to detect the positions of the edges of the bars and indeed, if desired, also the heights of the bars forming the marking 22. Such a scan enables the relative position of the second article 14 relative to the first article to be determined in one horizontal direction in FIG. 1 (the x-direction).

The cantilever 28 shown at the right in FIG. 1 is seen end on and is provided with a respective fine point 32 which is able to touch and scan the second marking 24 in a direction perpendicular to the plane of the drawing, i.e. in the y-direction, to determine its position relative to the second marking and thus the alignment of the second article 14 relative to the first in a second horizontal direction perpendicular to the first. These two alignments thus ensure that the second article is accurately aligned in juxtaposition relative to the first.

Moreover, since the heights of the bars of the markings 22 and 24 bear a known relationship to the height of the imprint area the amplitude of movement required to achieve the desired imprint can also be determined. This is, however, not essential since the imprint movement could also be force limited, i.e. carried out until a specific force is exerted on the first article 10 by the imprint stamp forming the second article 14.

It will be appreciated that the accuracy of the alignment is now dependent on four things:

A) The alignment of the surface relief markings on the first article with the imprint area or the pattern provided thereon. This alignment accuracy can be achieved to a high level by patterning the surface relief markings at the same time the imprint area is generated on the semiconductor wafer. Indeed it is not essential for the surface relief markings to have an exactly predetermined position providing their position relative to the imprint area can be accurately determined, which is also possible using atomic force microscopy or a similar process. This also means that the surface relief markings could be manufactured separately and subsequently bonded to the first article.

B) The alignment of the flexible structures 26, 28 on the second article 14 relative to the template 16. Precisely the same considerations apply here as given above in relation to the alignment of the surface relief markings 22, 24 with respect to the first article 10.

C) The accuracy with which the surface relief markings 22, 24 can be measured by way of their interaction with the flexible structures 26, 28. It is well established in the art of atomic force detectors that measurement accuracies of 1 nm or better can be achieved in a variety of ways.

D) The accuracy with which the second article 14 can be moved relative to the first 10. There are a variety of actuators which are known in the scientific community enabling movements with accuracies in the nanometer range. Such actuators include piezoelectric actuators, thermal actuators which operate by linear or differential thermal expansion, electromagnetic actuators, and oscillatory actuators.

In a practical embodiment the amplitudes of movement which can be achieved with actuators having accuracies in the nanometer range are restricted and therefore the apparatus of the present invention will generally have a first means for approximate, coarse positioning of one of said first and second articles 10, 14 adjacent to the other one as well as provision for at least restricted, fine, relative movement between said first and second articles. The actuators for movement in the range of several micrometers to one nanometer will be conveniently provided between the positioning means and the moved article, for example the second article 14.

In the present embodiment the second article is shown supported by two rods 34, 36 in two guides 38 and 40 respectively. The guides are connected to the table 12 as indicated by arms schematically indicated by the lines 42, 44 and are thus fixed relative to the first article 10. They could also be connected to the first article 10. Only two positioning/support means 34, 38 and 36, 40 are shown. In reality there have to be as many positioning means as are required to allow basic (coarse) positioning of the second article relative to the first (generally in at least one plane parallel to the corresponding confronting plane of the relevant oppositely disposed surface of the first article), which basic position may be checked using known optical alignment techniques. That is to say the positioning means has to permit positioning of the second article relative to the first in x- and y-directions, i.e. in the x-y plane. In addition either both coarse and fine positioning, or just fine positioning in the z-direction is necessary for the imprint process depending on how the apparatus is designed.

E.g., if the second article, i.e. the patterned mold is placed only a small distance above the first article, fine movement alone may be necessary to allow the imprint process to be carried out. However such close positioning may be difficult in practice, since the space for introducing the substrate is restricted, unless it is itself moved towards the patterned mold against a stop provided in the apparatus before alignment takes place. On the other hand if both coarse and fine positioning of the second article relative to the first may be appropriate to facilitate introduction of the substrate or wafer forming the first article beneath the patterned mold.

The positioning means must also allow adequate space for the handling of the second article relative to the first.

Figure 2:
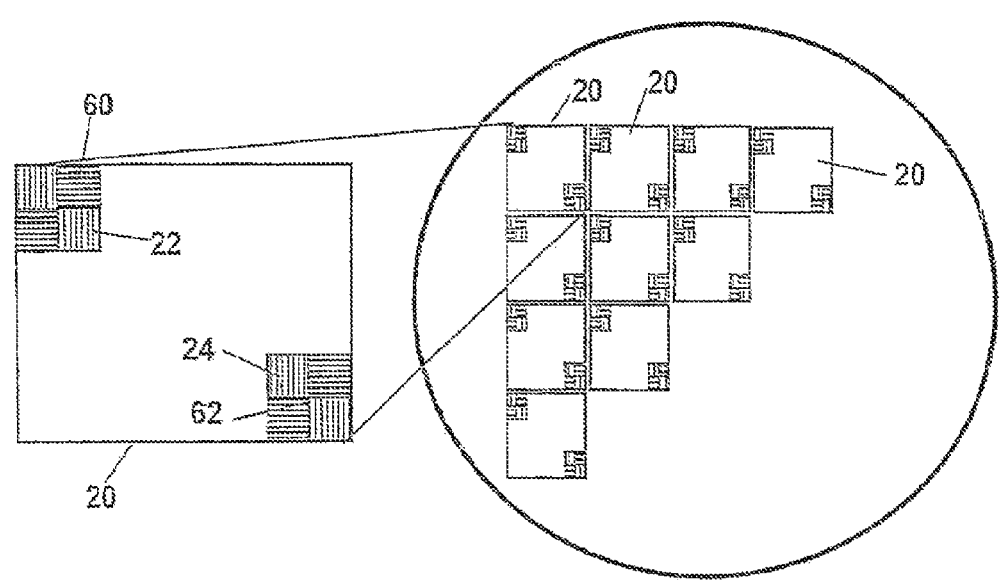
FIG. 2 shows a plan view of a semiconductor wafer having various imprint areas each with its own surface relief markings for use in the present invention.

In practice one stamp may be used to process a plurality of imprint areas 20 on one semiconductor wafer 10, see for example the plurality of imprint areas 20 provided on the semiconductor wafer of FIG. 2. In this case the positioning means has to allow for a relative movement of the template into coarse alignment with the individual imprint areas or groups of imprint areas if a group of imprint areas, say four imprint areas is to be subjected to imprint lithography at one time, which would be usual. Such positioning means are known per se they are used in conventional semiconductor processing.

In accordance with the present teaching actuators such as 46, 48 forming fine positioning means with accuracies in the nanometer range are incorporated between the coarse positioning means and the second article so that once coarse positioning has been achieved the actuators can be energized to carry out scanning movements of the second article 14 with the flexible structures 26 and 28 relative to the surface relief markings 22, 24. Once the precise position of the alignment marks has been determined the actuators 46, 48 can then be used, i.e. controlled to accurately position the second article relative to the first with reference to the alignment marks. Alternatively the actuators can be used solely for fine alignment and the scanning movements of the flexible structures can be effected by separate actuators disposed on the flexible structures or between the flexible structures and the second article to generate the required scanning movement.

FIG. 2 shows that the surface relief markings can also be provided on the imprint areas 20 themselves and shows two surface relief markings 22, 24 for each imprint area 20. In this case the surface relief markings 22, 24 are provided in diametrically opposite corners of each imprint area. This is not essential, they could for example be provided in all four corners. Only a single surface relief marking is necessary if its topology is chosen so that accurate alignment can be achieved with reference to that one marking. In such a case only a single flexible structure is necessary. FIG. 2 also shows that a marking 22, 24 divided into four quadrants with differently orientated bars in each quadrant can be used for a surface relief marking. This is only one of an infinite number of possibilities. It will however be understood that it is relatively straightforward for a flexible structure configured in the manner of a probe for an atomic force microscope to find the center of the marking shown and to use its coordinates (or the coordinates of a different position of the quadrant) for the precise alignment of the second article 14 relative to the first 10. In fact it is preferable to use surface relief markings of the kind shown in FIG. 2 in the embodiment of FIG. 1 in which simplified markings were chosen to simplify the explanation but would not readily allow accurate rotational alignment around the z-axis. Such rotational alignment can be achieved with the markings 22 and 24 shown in FIG. 2 (and also with a whole variety of other markings).

Returning now to FIG. 1 the manner of operation can now be readily understood. As mentioned above coarse positioning is first effected. This can be done manually or by computer control using the computer in the form of the suitably programmed microprocessor 50 which obtains positioning data from the memory 52 and can also make use of optical positioning information from auxiliary systems to steer the movement of the second article 14 relative to the first article 10. For this the second article 10 has to be mounted in a mechanism or carriage such is used in the fields of metrology or machine tools for movement of a probe or machining tool to a specific point in a coordinate system and to provide the probe or machining tool with a desired spatial orientation. The positioning/support means schematically illustrated by the reference numerals 34, 38 and 36, 40 in FIG. 1 can be realized in accordance with any known system for the accurate handling of probes or machining tools or other items in a coordinate space. The optical positioning information can, for example, come from optical positioning systems known per se in the semiconductor field, for example in connection with the existing S-FIL process. Also glass measuring rod or other scale systems used in metrology and in machine tools can be used for basic positioning of the second article relative to the first.

Once basic positioning has been achieved the basic positioning means is locked and actuators such as 46 and 48 are actuated to produce scanning movement of the flexible structures 26, 32 to determine the precise relative position of the second article relative to the first. The readout signals from the detectors associated with the flexible structures are amplified by a preamplifier 54 and fed to the microprocessor 50. The microprocessor 50 analyses the signals from the actuators and compares them with reference information stored in the memory 52 relating to the topology of the surface relief markings 22 and 24 and their positions relative to the imprint area 20.

Since the microprocessor 50 also has information concerning the relative positions of the flexible structures relative to the template 16 it is able, from the result of the comparison, to issue positioning commands to the actuators 46, 48 to accurately align the flexible structures with the surface relief markings, for example to align the tips 30 and 32 with the centers 60 and 62 of the markings 22, 24 of FIG. 2, and thus to accurately align the second article 14 with the first 10 and the template 16 with the imprint area 20 and any pattern already provided thereon.

Thus the microprocessor 50 generates, via the template stage position control 58 for the actuators, in this example piezomotors 46 and 48, steering signals for steering at least one of said first and second articles relative to the other to achieve said desired alignment. Thus the template stage position control 58 forms steering means in the sense of the present invention. It could naturally also be integrated into the microprocessor 50. The reference numeral 57 relates to a keyboard which can be used to input information into the system and the reference numeral 59 indicates a screen which can provide user guidance menus and display other information useful to the user. The items 50, 52, 54, 57, 58 and 59 can all form part of a computer workstation or PC associated with the apparatus.

The signals obtained from the flexible members are described later with reference to FIGS. 17 to 24. After alignment of the first and second articles has been completed the imprint step is carried out by movement of the first article (i.e. the template or patterned mold) towards the second article (i.e. the substrate), or vice versa, by means of a suitable actuator acting on the second article (or the first article), so that the template enters into contact with the moldable film formed on the substrate. Once the imprint step has been completed the imprint tool forming the second object 14 can be moved to a different intended imprint area 20 on the first object 10, as illustrated in FIG. 2 and the alignment process and imprint steps can be repeated there, using the surface relief markings at the new imprint area 20. This process can be repeated as many times as required.

It is not essential to recheck the alignment for each imprint area, although this can be done and will frequently be done. It is also considered sufficient if the alignment is only checked for some of the imprint areas on the first object 10. For this possibility to be realized it is necessary to use a positioning/support system with high inherent accuracy. For example, such systems are known from the fields of metrology and precision engineering which use interferometry to achieve a high positioning accuracy which can approach the levels required here. Thus, once the correct alignment has been found for one imprint area it can be retained for one or more further imprint operations. I.e. a type of step and repeat method can be used.

It should be noted that despite the existence of such highly precise positioning systems they cannot be used to find the correct initial alignment, since the data for this, i.e. the correct initial position for the second object 14 relative to the first 10 has first to be found using the flexible structure approach of the present invention.

If adequately high precision positioning systems with a suitable amplitude of movement can be found, then they could be used both for basic positioning and for the nano-range positioning. I.e. they could be used instead of the nano-range actuators such as 46, 48 for scanning movement of the second object 14 and flexible structures 26, 28 relative to the first object.

Turning now to FIGS. 3, 4, 5 and 6 a method will be described for the manufacture of a second article having flexible structures provided thereon.

Figure 3:
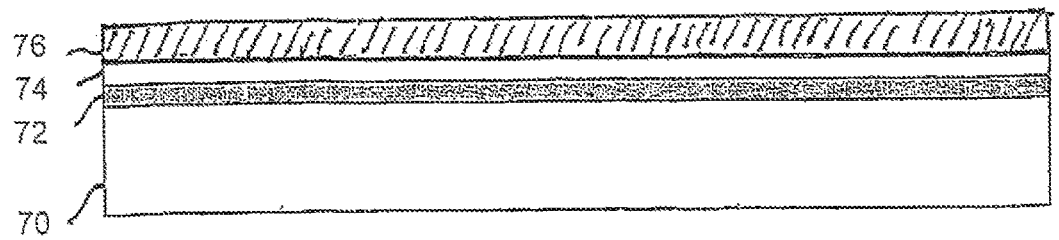
FIG. 3 shows a silicon structure forming a starting point for manufacturing a second article in accordance with the present invention.
Figure 4:
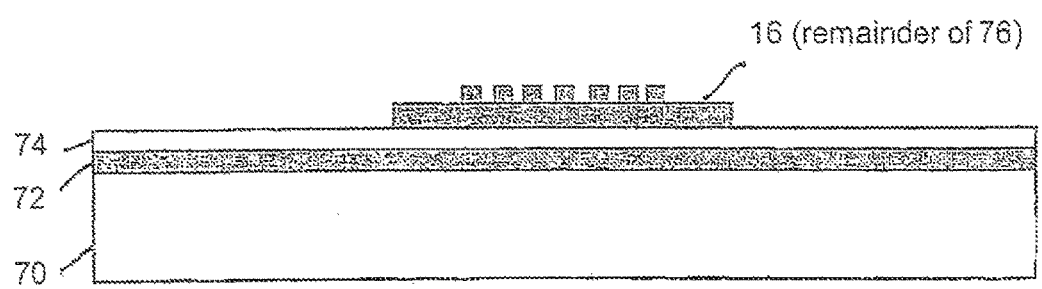
FIG. 4 shows the silicon structure of FIG. 3 after formation of a template thereon.
Figure 5:
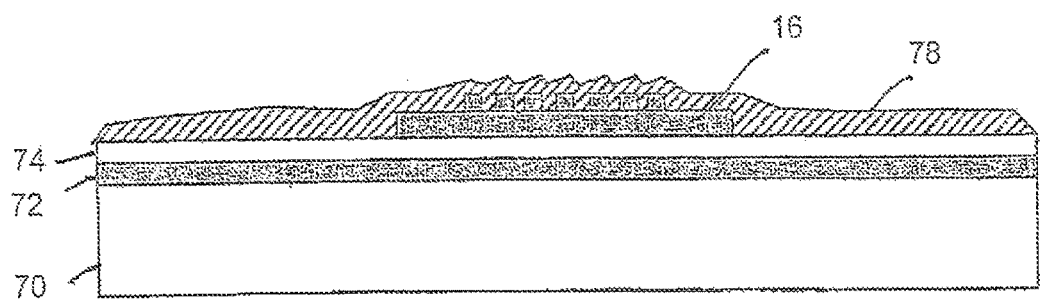
FIG. 5 shows a step for the protection of the template of FIG. 4.

FIG. 3 shows a starting wafer comprising a silicon wafer 70 having a layer of silicon dioxide (Siθ2) 72 followed by another layer of epitaxial silicon 74 and a top layer of SiO2 (quartz) 76. Such wafers are commercially available as SOI wafers. Using such a wafer, a layer of chromium is then deposited on the exposed surface of the upper layer 76, typically by a sputtering technique. A layer of photoresist is then applied to the chromium layer and is patterned using an electron beam to locally expose the photoresist layer. The exposed photoresist layer is then developed and this enables the chromium to be etched away locally to expose the underlying layer of silicon dioxide 76. The remaining photoresist covering the chromium that has not been etched away is then removed. Thereafter, the exposed layer of silicon dioxide 76 not covered by the chromium can then be etched away using dry etching. The areas underlying the remainder of the chromium layer are protected. The remainder of the chromium layer is then removed. This leads to the structure shown in FIG. 4 where the silicon dioxide layer has been etched to form the desired template 16, the raised island shown at the top in FIG. 4, and has been removed completely to the left and right of the template 16 to expose the underlying silicon material of the layer 74. The template has now been finished and the entire wafer is covered at the exposed upper surface with a layer 78 of silicon nitride ($Si_xN_y$) as shown in FIG. 5.

Figure 6:
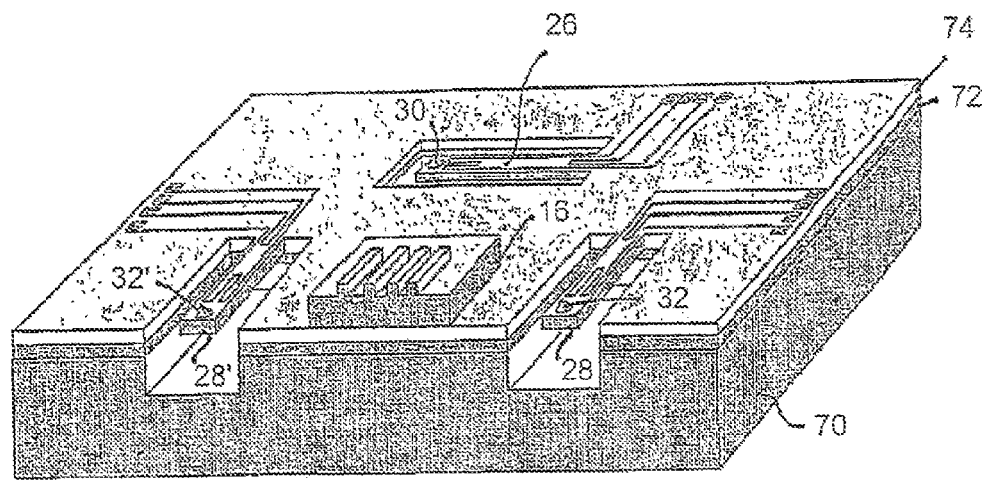
FIG. 6 shows a first variant of the silicon structure of FIG. 4 after the formation of the flexible structures thereon.

Next, the flexible structures in the form of cantilevers 26, 28 are formed in the wafer 70 using known fabrication procedures, for example the fabrication procedure for cantilever beams outlined in the paper L W. Rangelow et al, Proc. SPIE 2879, 56 (1996), This results in a structure such as is shown in FIG. 6. In actual fact, FIG. 6 has had the first part of the wafer in front of the plane of the drawing removed and in practice a fourth cantilever corresponding to the one 26 at the top of the drawing of FIG. 6 is provided symmetrically on the other side of the template 16 (which is itself sectioned in the drawing). As mentioned, the fabrication of the cantilevers is described in the above named paper by L W. Rangelow et al. It is also described in the German patent application DE 103 03 040 A1 and in the article first referenced in this application (J. Vac. Sci. Technol. B 21(6) November/December 2003, pages 3102 to 3107). As can be seen from FIG. 6, the flexible structures here have the form of cantilevers 26, 28 and 28' which are basically made in the silicon layer 74 of the wafer 70 and which are only fixed to the wafer at one end. The tips 30, 32 and 32' can be integrated into the silicon material and formed at the beginning of the micro-machining used to form the cantilevers, or can be electron-beam deposited tips made after the fabrication of the cantilever beam and grown directly on an aluminium micro-heater which is incorporated into the cantilever structure as part of the bimorph actuator used to adjust the vertical position of the tip of the cantilever. With this arrangement of the cantilevers four surface relief markings would typically be provided, one at the middle of each side of a square imprint area 20.

In one example the silicon wafer used is a silicon-on-insulator wafer of 3" diameter comprising a 40 μm thick Si-layer 74 (12 Ohmcm n-type silicon <100> orientation) bonded to a 70 nm thick thermal oxide layer grown on <100> base silicon wafer. The oxide layer 72 is used as an etching stop layer. If the silicon tip has to be integrated on the cantilever, a thermal oxide needs to be grown and patterned to form an 8000 Å thick mask which is subsequently used for wet etching of the Si tip. After a standard RCA clean, an 8000 Å thick oxide is grown. This film is patterned and the resist mask over the oxide is employed as a mask for the boron contact implantation at $1.1 \times 10^{15}$ $cm^2$, 30 keV. This resist mask is then removed using m-wave plasma stripping and this is followed by growth of passivating thermal oxide during a 1 h anneal at 900° C. Using a resist mask again, the piezoresistors incorporated in the sensor system associated with the cantilevers are configured in a Wheatstone bridge configuration defined in the oxide layer and boron implanted at $4 \times 10^{14}$ $cm^2$ 20 keV, followed by growth of passivating thermal oxide during annealing at 1050° C. for 30 minutes. The cantilevers are then patterned and plasma-etched to open contact holes to the highly doped areas. Aluminium for the contacts to the piezoresistors in the metal layer forming the micro-heater and bimorph actuators is then deposited and annealed in a forming gas at 410° C. for 50 minutes. The oxide layer on the back of the wafer is patterned and a gas chopping reacted ion etching process (GChRIE) combined with KOH wet step is used to release the cantilever membranes and partially dice the wafer. The buried oxide used to stop the silicon etch is then removed with a buffered oxide etch solution, using a mechanical wafer chuck to protect the topside of the cantilevers. To form the cantilever beam and to cut up the single sensor chip employing GChRIE step, a thick resist mask is used. Finally, the resist mask is removed in oxygen plasma.

Thus, in FIG. 6, the template 16 is integrally incorporated on the wafer with the flexible structures in the form of cantilevers 26, 28, 28'. It is, however, also possible to form the template 16 separately and to incorporate it into the wafer 70 by forming a suitable recess in the wafer and bonding the template in place using a convenient means, such as, for example, an adhesive. This is shown in FIG. 7 where the separate template 16 is received in a well 82 of the wafer 70.

Figure 7:
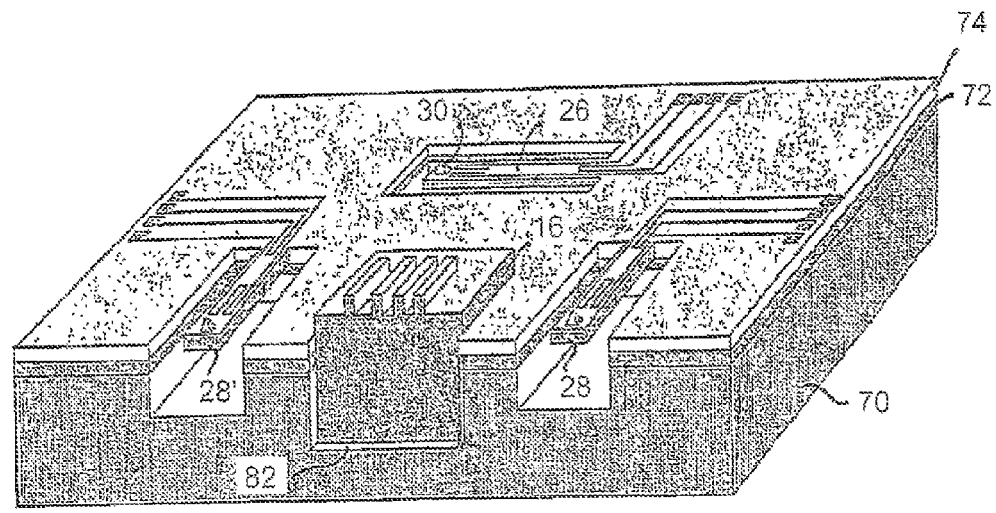
FIG. 7 shows a variant of the silicon structure of FIG. 6.
Figure 8:
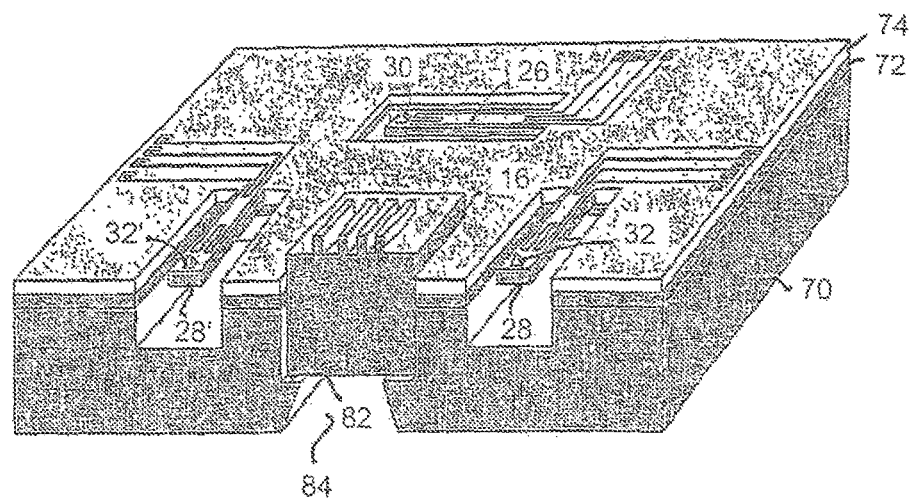
FIG. 8 shows a further variant of the silicon structure of FIG. 6

Another possibility which builds on the construction of FIG. 7 is shown in FIG. 8. Here, the wafer is removed at 84 at the base of the well 82 and this has the advantage that an optical system can be used to view the first article through the transparent template 16 for basic alignment purposes and also for the purpose of exposing the photocurable layer during nanoimprint lithography.

Figure 9:
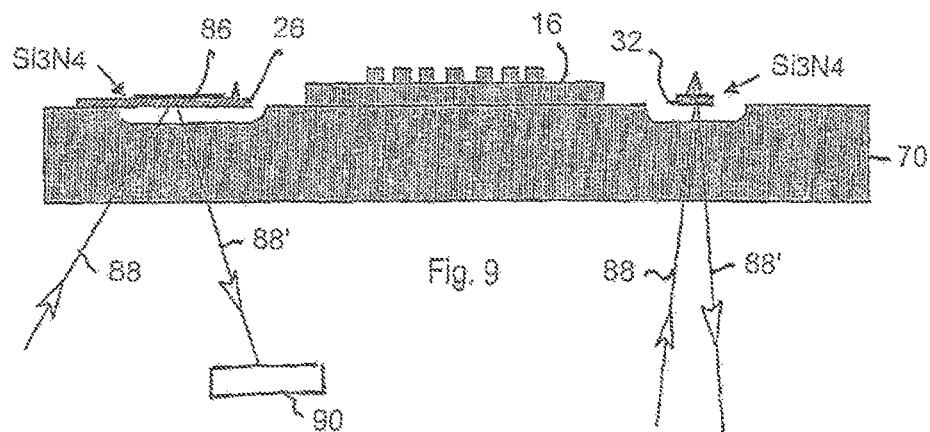
FIG. 9 shows an optical detector used in conjunction with a structure resembling that of FIG. 6.
Figure 22:
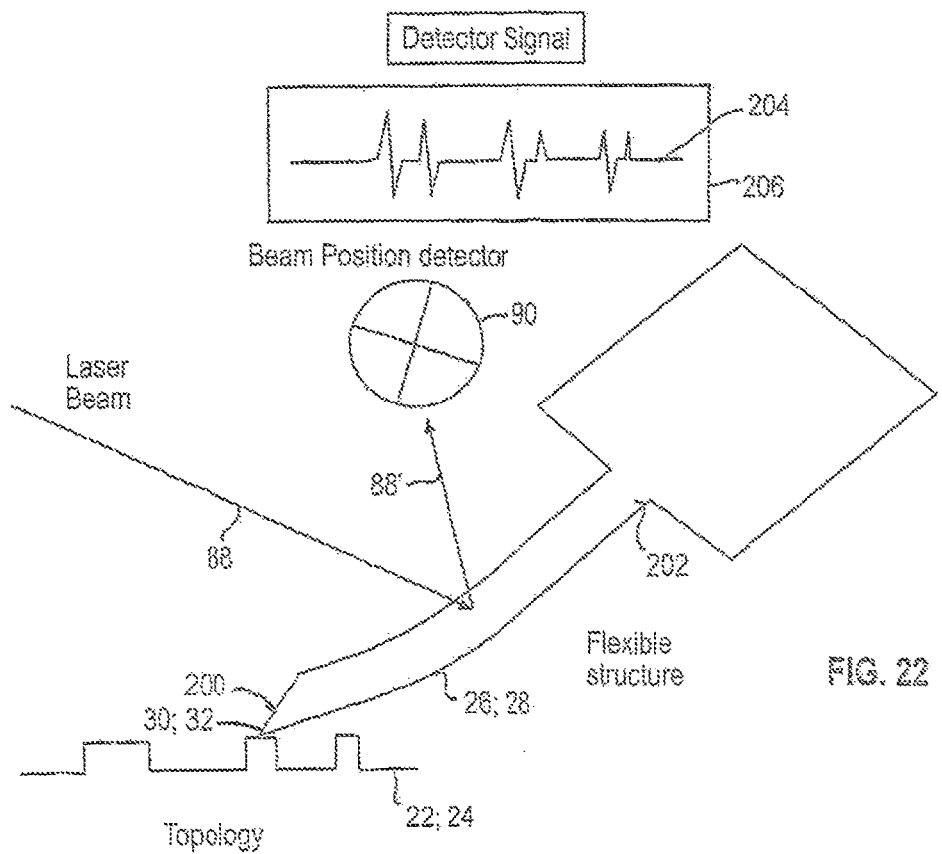
FIG. 22 illustrates an embodiment of a flexible structure similar to that of FIG. 9 used as a contact detector in which detection of the deflection of the flexible structure at the edges of an alignment mark is effected by utilizing a laser beam reflected at the flexible structure and a beam position detector.

One possibility for detecting the contact of the flexible structure, i.e. the tip thereof, with the edges of the alignment mark is shown in FIG. 9. This embodiment uses optical detection of the deflection of the flexible structures 26, 28 due to the interaction with the surface relief markings 22, 24 on the first article. This system is illustrated in FIG. 9. A reflective layer 86 is provided on the surface of the cantilevers 26, 28 and respective optical beams 88 are used to measure the deflection of the cantilevers, which changes the angle of reflection of the respective reflected rays 88'. A suitable detector, for example a position sensitive photosensor or a finely resolving linear photodiode array 90, can be used to measure the angle of reflection of the light reflected at the reflected layer on the cantilevers. This provides a very accurate measurement because the angular deflection of the cantilever is effectively amplified by the movement of the reflected light beam. Reference should also be made here to FIGS. 22 to 24 which further illustrate the detection of the edges of an alignment mark such as 22 or 24 by moving or "dragging" a flexible structure, here with a free end forming a tip 30 or 32 rather than a pointed formation projecting from an otherwise flat arm, which is not strictly speaking necessary, across the alignment mark in accordance with the arrow P shown in FIG. 23. FIG. 22 shows how the beam of light 88 from a laser strikes the flexible structure, in this case at a position away from the end of the flexible structure intermediate its free end and its more rigidly mounted end 202, where it adjoins the wafer carrying the template or a mounting base used to attach it to the wafer carrying the template.

Figure 23:
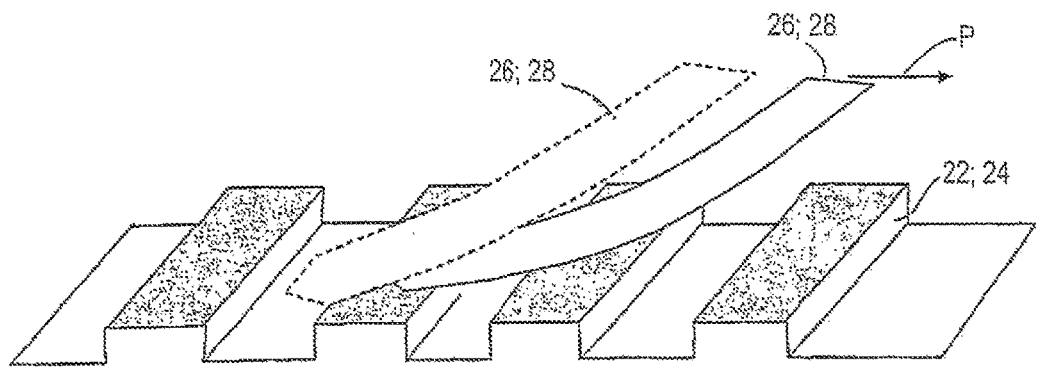
FIG. 23 illustrates the deflection of the flexible structure of FIG. 22 in a perspective view and FIG. 24 shows how the beam position changes as a function of the deflection of the flexible structure of FIGS. 22 and 23.
Figure 24:
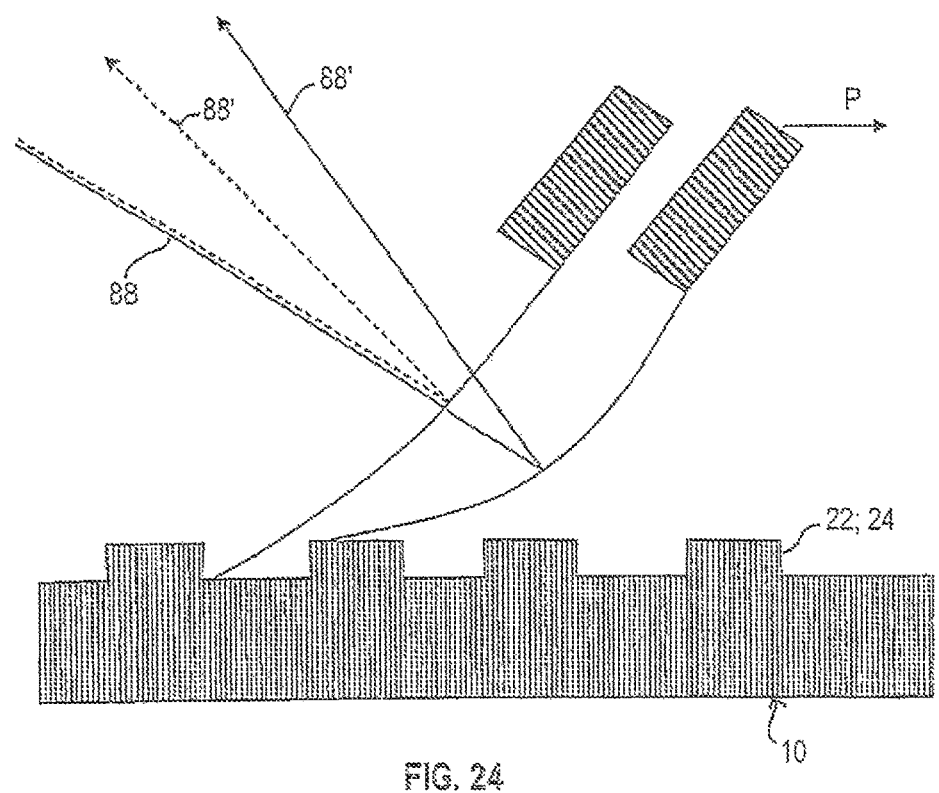

As can be seen from FIGS. 23 and 24 the bending deflection of the flexible structure changes each time the flexible structure moves over an edge of the alignment mark or into contact with a base portion thereof between two raised bars and this changes the angle of reflection of the reflected light beam 88' (FIG. 24) so that the signal 204 from the position sensitive detector changes as illustrated in the inset 206 of FIG. 22. the edge positions can be seen quite clearly in the detector signal and their spacing in time accurately reflects the physical spacing of the edges at the speed of scanning movement of the flexible structure. From this the relative position of the alignment mark can be found accurately An absolute measurement of the position of the edges is not essential, the shape of the signal can itself be used to determine the relative alignment, this can be done very fast. It will be noted that FIG. 23 shows two different positions of the flexible structure, one in dotted lines and one as solid line. FIG. 24 shows the corresponding reflected light beam 88' again once in dotted lines and once in a solid line.

Figure 10:
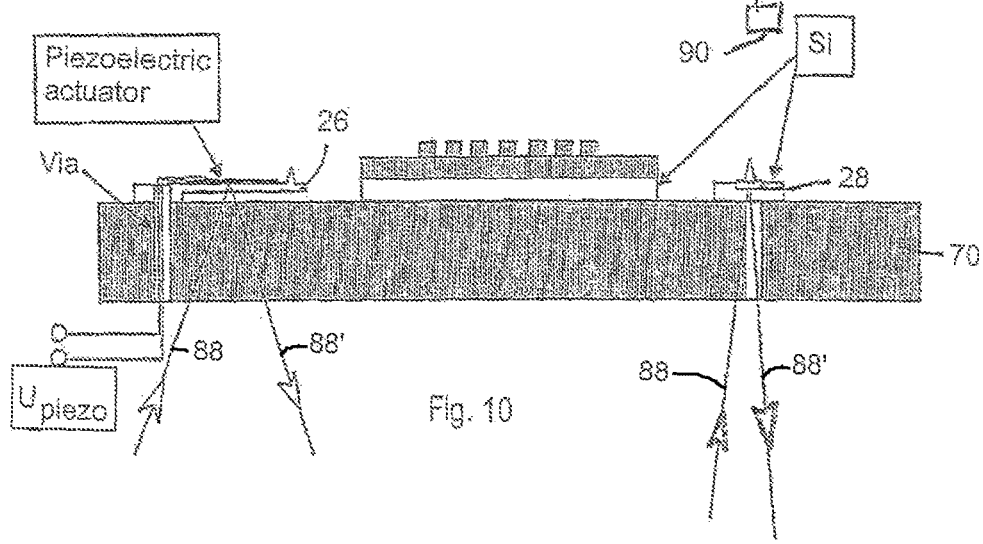
FIG. 10 shows a variant of the structure of FIG. 9.

FIG. 10 shows an arrangement similar to FIG. 9 but in this case the template 16 and the cantilevers 26, 28 are formed separately from the wafer 70 and subsequently joined to it by adhesive bonding. FIG. 10 also shows the use of an integrated piezoactuator on the cantilever beam to move the cantilever beam in the z direction.

Figure 11:
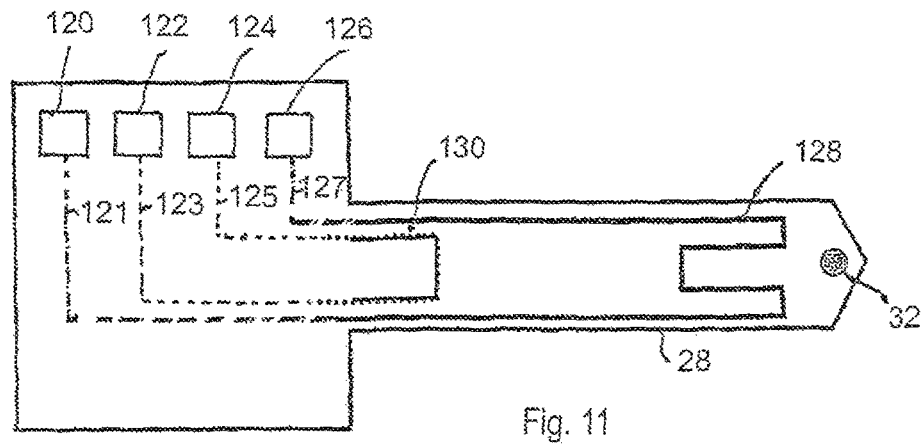
FIG. 11 shows schematically and not to scale a plan view on a flexible structure such as is illustrated in the form of a cantilever in any of the FIGS. 6, 7 and 8.
Figure 12A:
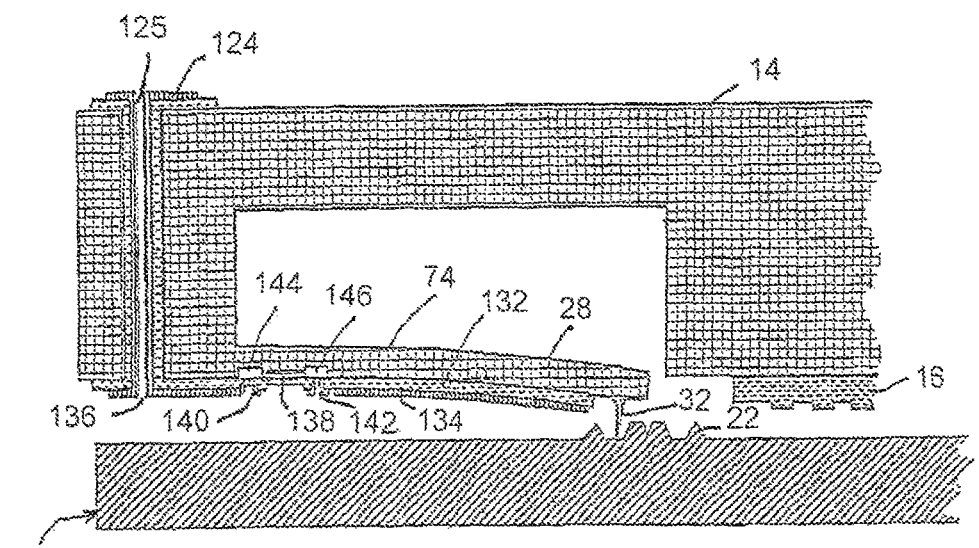
FIG. 12 shows in FIG. 12A a detailed cross-section through a typical cantilever useful in practice in a first deflected position and in FIG. 12B the same cantilever in a second retracted position.
Figure 12B:
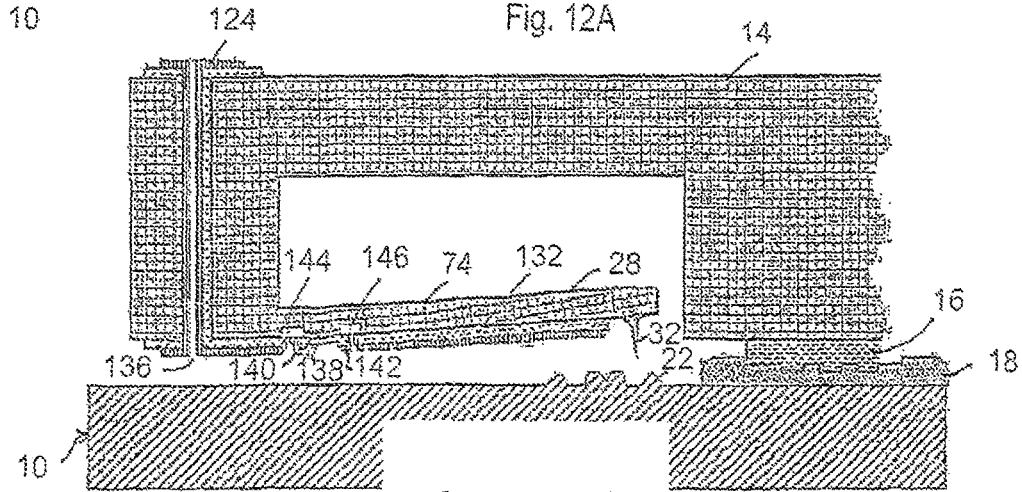

FIG. 11 shows a plan view of the surface of a cantilever 28 such as is illustrated schematically at three positions in each of FIGS. 6, 7 and 8, however with the difference that the contacts 120, 122, 124 and 126 and the associated leads 121, 123, 125 and 127 are now provided on the other side of the wafer 14, i.e. at the top in FIG. 11 and in FIGS. 12A and 12B corresponding to the bottom of the wafer in FIGS. 6, 7 and 8. This is the reason the leads are shown in broken lines as are the outlines of the contacts. Two of the four electrical contacts 120, 122, 124 and 126, more specifically the contacts 120 and 126 are connected to a bimorph actuator 128 via respective leads 121 and 127. The other two contacts 122 and 124 are connected to a Wheatstone bridge circuit comprising four piezoresistors (not shown in FIG. 11) forming a piezoresistive sensor 130 via respective leads 123 and 125.

The design of the bimorph actuator 128 and the piezoresistors can be seen in more detail from FIGS. 12A and 12B. The bimorph actuator is formed by the Si layer 74 of the cantilever 28, by an additional overlaid layer 132 of SiO2 and by an Al layer 134 provided on top of the SiO2 layer 132. The aluminium layer 134 is patterned to form two leads leading via respective via-holes in the wafer 14 to the contacts 120 and 126 which are provided on the top surface of the silicon wafer 14 in FIGS. 12A and 12B but not shown in the section plane of FIGS. 12A and 12B. Although the via-holes associated with the leads 121 and 127 to the contacts 120 and 126 are not shown in FIGS. 12A and 12B these figures do show a via-hole 136 associated with a lead 125 to the contact 124 associated with the Wheatstone bridge detection circuit and the piezoresistor 138. The lead 123 to the contact 122 is also not shown in FIGS. 12A and 12B.

As described in the above referenced article (J. Vac. Sci. Technol. B 21(6) November/December 2003, pages 3102 to 3107) the three layers 74, 132 and 134 form a bimetallic (Si 74/Al 134) structure which can be deflected by applying power from a suitable power supply via the contacts 120 and 126 to the aluminium layer 134. More specifically the cantilever with the integrated bimorph actuator is normally bent to or beyond the advanced position shown in FIG. 12A due to residual stress created during the deposition of the bimorph actuator.

DC heating power applied to the aluminium layer can be used to cause differential expansion of the bimetallic structure so that the cantilever can be retracted into the position shown in FIG. 12B in which the tip 32 lies behind the front face of the template 16 permitting the printing operation in which the template 16 is used to pattern a layer of imprint resist 18 deposited on the imprint area 20 of the first wafer 10.

The sensing operation, by which the tip 32 of the cantilever is used in an advanced position in which it projects beyond the front face of the template 16 (the lower side of the template in FIGS. 12A and 12B), to touch and sense the surface relief marking 22, without the template contacting the first article, can either be a natural advanced position of the cantilever or an advanced position controlled by the supply of dc heating power to the aluminium layer 134. Thus the cantilever tip 32 is just beyond the front face of the template 16 and is able to touch the surface of the first article 10 in accordance with the preferred sensing mode of the invention.

The Al layer 134, the SiO2 layer 132 and the Si layer 75 can be patterned not just for the formation of the via-holes such as 136, which are lined by the SiO2 layer 132 and the Al layer 134 but also to define four piezoresistors such as 138 (only one shown) and the Al leads connecting them together in the Wheatstone bridge configuration and the contacts 122 and 124 via the respective leads such as 125 passing through respective via holes such as 136.

Each piezoresistor comprises a p+ boron doped portion of the Si layer extending between two p++ boron doped electrodes 144 and 146 contacted by Al contacts 140 and 142 formed by regions of the Al layer 134. The precise patterning is selected so that the piezoresistors are electrically separated from the bimorph actuator and the associated leads and contacts.

Figure 13A:
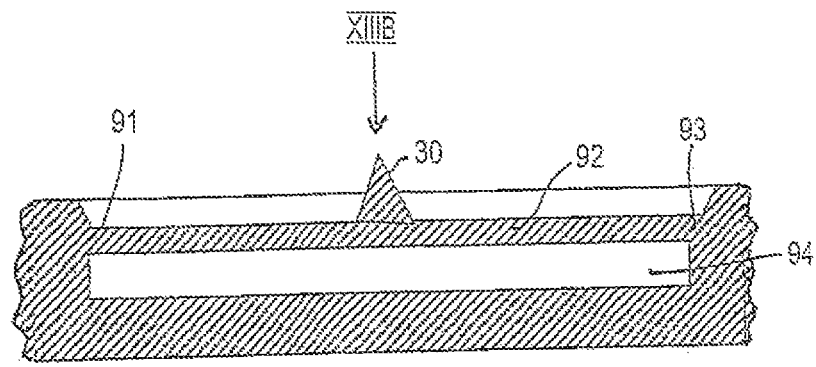
FIG. 13 shows in schematic form an alternative flexible structure in the form of a flexible bridge formed in a portion of a wafer and supported at two points, with FIG. 13A showing the bridge in a longitudinal section in accordance with the section plane XIIIA-XIIIA of FIG. 13B and FIG. 13B showing the bridge in plan view in accordance with the arrow XIIIB of FIG. 13 A.
Figure 13B:
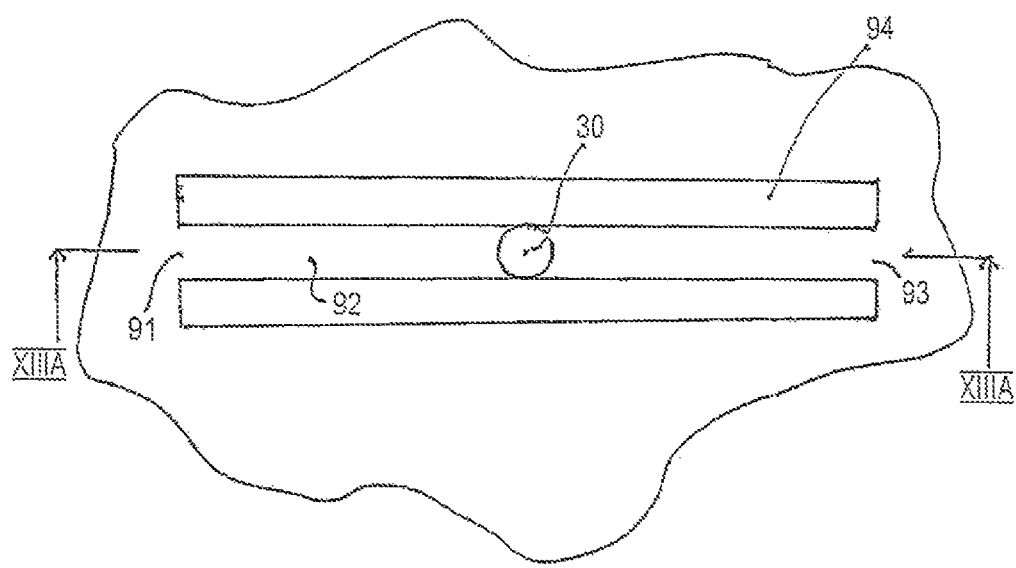

Turning now to FIGS. 13A and 13B there can be seen an alternative type of flexible structure in the form of a bridge. It can be seen that the bridge 92 carrying the tip 30 is supported at both ends 91, 93 in the silicon wafer 70, and that a cavity 94 is formed on both sides of the bridge and underneath the bridge to allow for deflection of the tip of the cantilever in the z direction.

Figure 14A:
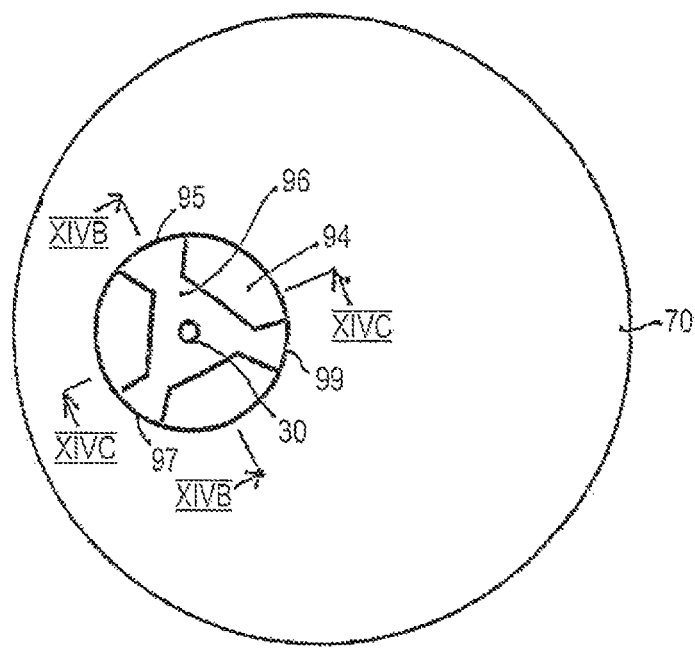
FIG. 14 shows an alternative flexible structure in the form of a flexible membrane supported at three points, with FIG. 14A showing in a schematic representation, not to scale, a part of a wafer provided with the membrane in plan view and FIGS. 14B and 14C showing cross sections on the section planes XIVB-XIVB and XIVC-XIVC respectively.
Figure 14B:
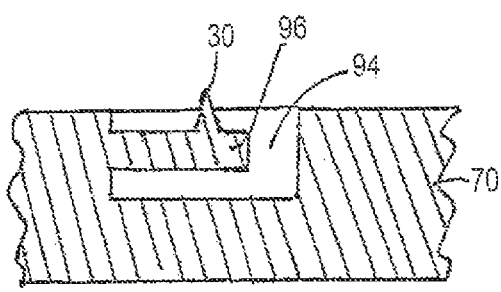
Figure 14C:
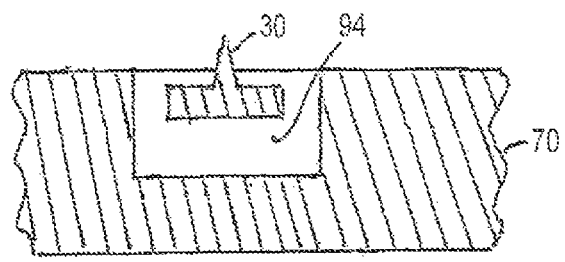

FIG. 14A shows another alternative form of flexible structure, here in the form of a membrane 96 supported at three points 95, 97, 99 on the silicon wafer 70. The sections of FIGS. 14B and 14C show that the silicon material around the flexible membrane is removed to allow it to deflect in the z direction as is required to determine interaction with the first article. i.e. the membrane again sits in a cavity 94.

Figure 15A:
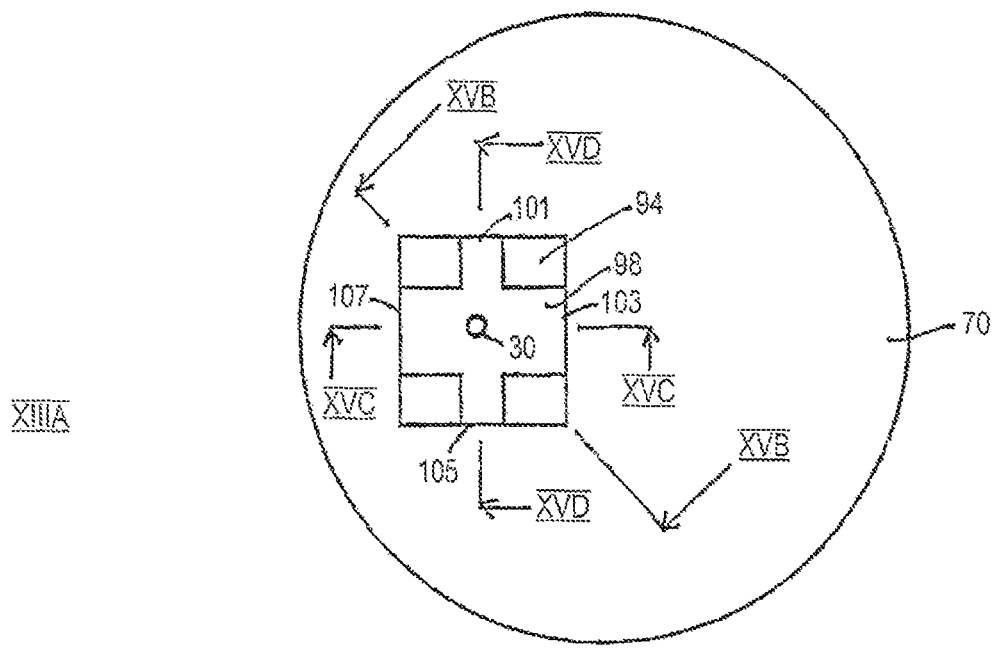
FIG. 15 shows an alternative flexible structure in the form of a flexible membrane supported at four points, in representations FIGS. 15A, 15B and 15C corresponding to those of FIGS. 14A, 14B and 14C.
Figure 15B:
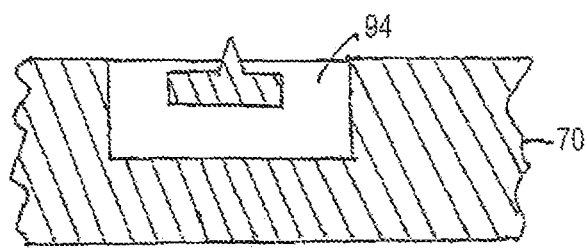
Figure 15C:
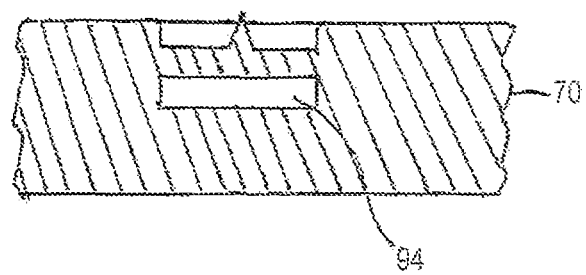

FIG. 15 shows a membrane 98 which is supported on the silicon structure at four points 101, 103, 105 and 107 and again it can be seen from the sections 15B and 15C that the silicon material is removed around the flexible membrane to permit deflection in the z direction. Section XVD-XVD is the same as the section XVC-XVC shown in FIG. 15C.

Figure 16:
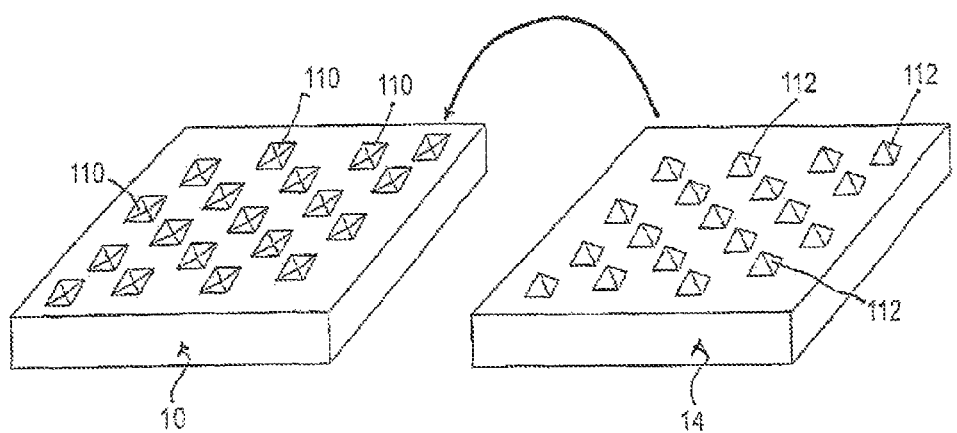
FIG. 16 illustrates the use of the invention in the chemical or biological field.

Finally, FIG. 16 shows a use of the present invention in a field other than that of semiconductor manufacture. In FIG. 16 the first article 10 takes the form of a wafer with a plurality of recesses 110 formed therein into which a chemical or biological reagent or sample can be introduced. The reference numeral 14 shows a second article, which is another wafer having an array of points 112 provided on it in a pattern complementary to those of the recesses of the first article 10. A chemical or biological sample or reagent can be provided on each of the points. If the second article 14 is then inverted and placed on top of the first article 10, then, if the alignment is correct, the tips of the points 112 on the second article 14 enter into the recesses 110 in the first article 10 and the biological or chemical reaction that is being investigated can take place. It will be appreciated that the surface relief markings and the flexible structures described in detail above will be respectively provided on the first article 10 and on the second article 14 to achieve the desired precise alignment. A similar technique can be used to align a detector for readout of the reaction. I.e. the detector would form a further first or second article, depending on where the readout is to be effected, i.e. at the second article or the first article. This detector could also be integrated into the first or second article.

In this specification the same reference numerals have been used in several of the drawings and the description given in connection with one drawing will be understood to apply to the items marked with the same reference numeral in other drawings unless something is stated to the contrary.

Turning now to FIGS. 17 to 21 some further examples will be given for ways in which a flexible structure can be used in a touching mode to quickly retrieve signal information relating to contact of the flexible structure 26 or 28 with edges of an alignment mark 22 or 24.

Figure 17:
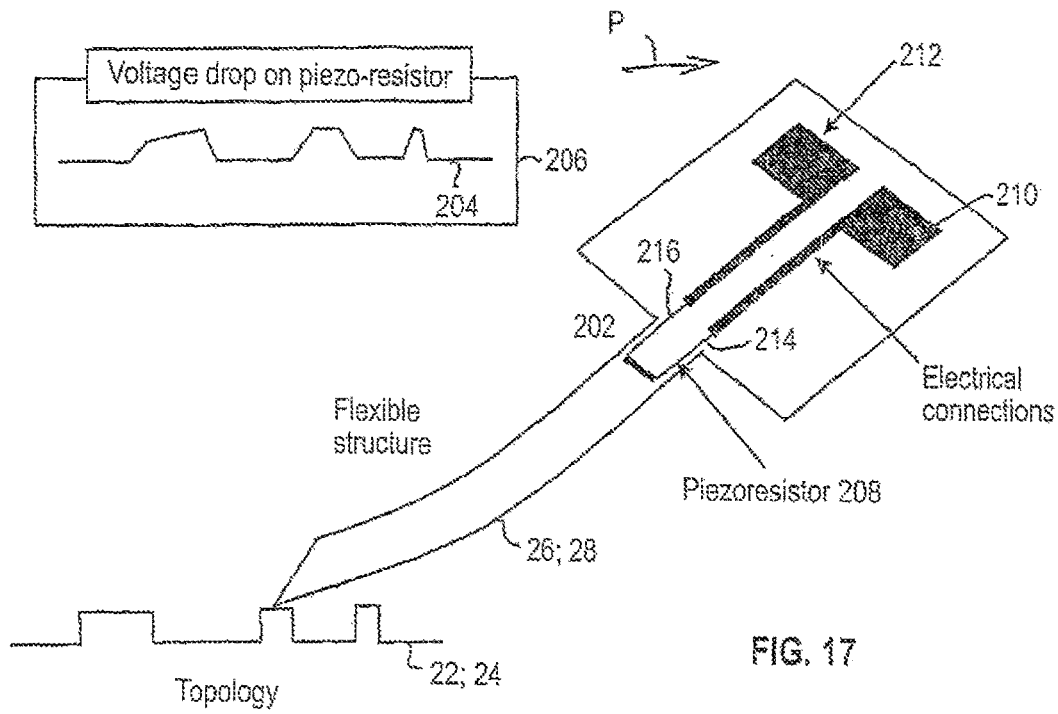
FIG. 17 illustrates one embodiment of a flexible structure used as a contact detector in which detection of the deflection of the flexible structure at the edges of an alignment mark is effected by measuring the voltage drop on a piezoresistor formed on the flexible structure.

In FIG. 17 a piezoresistor 208 is formed on the flexible structure adjacent its base 202 and bending deflection of the flexible structure leads to strain at its has 202 which results in a change in the resistance of the piezoresistor. This is detected by the voltage drop which occurs when a voltage is applied across the piezoresistor from two pads 210 and 212 provided on the wafer which are connected to the piezoresistor vial appropriate leads 214, 216. Again the shape of the voltage drop reflects the positions of the edges of the alignment mark. It will be noted that these edges are not uniformly spaced and this facilitates easy recognition of the precise relative position of the alignment mark.

Figure 18:
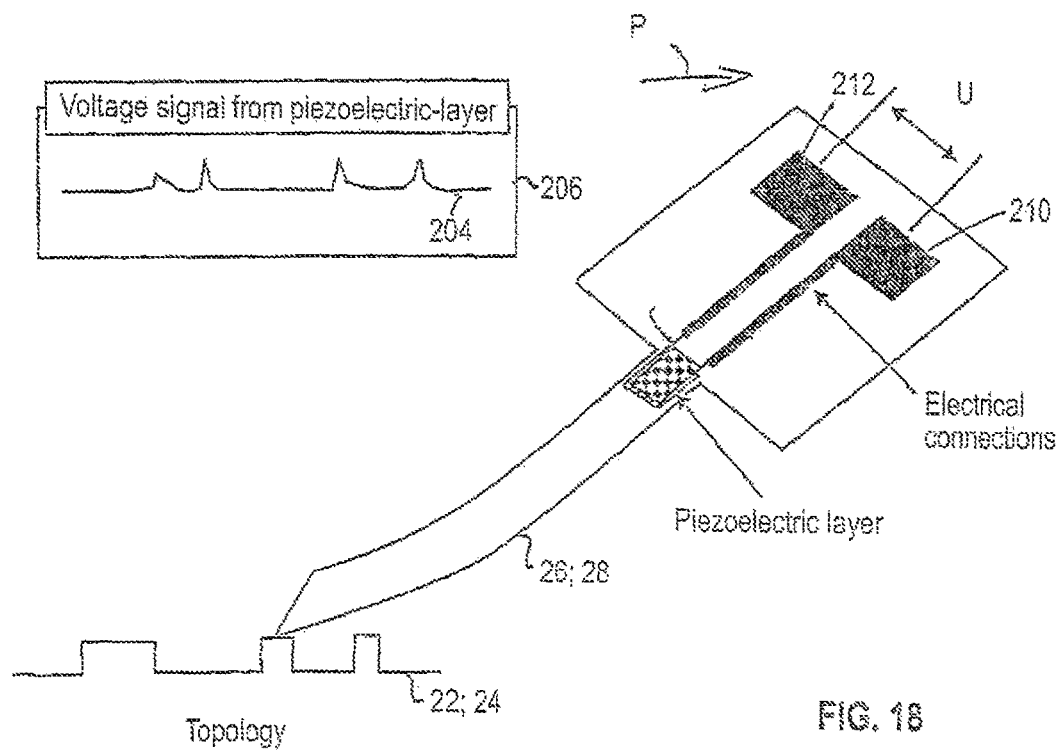
FIG. 18 illustrates another embodiment of a flexible structure used as a contact detector in which detection of the deflection of the flexible structure at the edges of an alignment mark is effected by measuring the voltage signal from a piezoelectric layer formed on the flexible structure.
Figure 19:
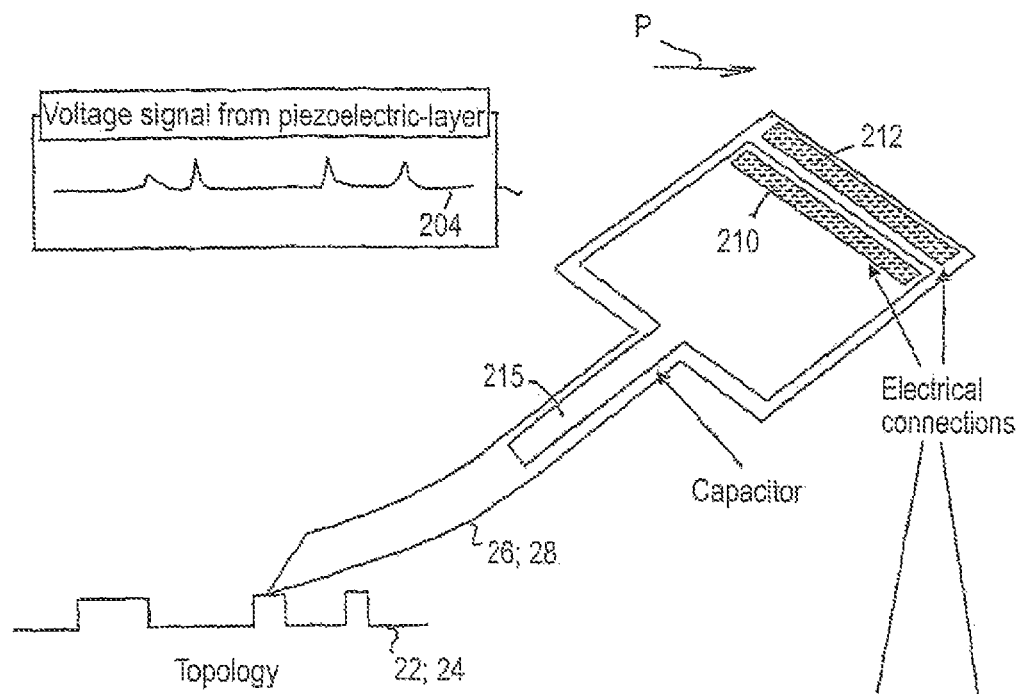
FIG. 19 illustrates a further embodiment of a flexible structure used as a contact detector in which detection of the deflection of the flexible structure at the edges of an alignment mark is effected by measuring the change in capacitance of a capacitor formed on the flexible structure.

The arrangement of FIG. 18 is rather similar to that of FIG. 17 except that here the piezoresistor is replaced by a piezoelectric layer. On deflection of the flexible structure 26 or 28 at the edges of the alignment mark 22 or 24 the voltage across the piezoelectric layer, which can be picked up, i.e. measured, at the electrodes 210 and 212, changes as a function of the change in strain resulting from the bending deflection. Again the position of the edges of the alignment mark can be determined from the voltage signal 204.

The arrangement of FIG. 19 is again rather similar to those of FIGS. 17 and 18, except that here a varying voltage signal 204 is detected as a result of a change in capacitance resulting from the bending deflection of the flexible structure as it flexible structure 26 or 28 travels across the edges of the alignment mark 22 or 24 during scanning movement in the direction P. This bending deflection of the flexible structure, which forms one plate or electrode 213 of the capacitor, results in a change of its distance from a conductive element 215 forming the second plate or electrode of the capacitor which is spaced from the first electrode or plate by an insulator 217.

Figure 20:
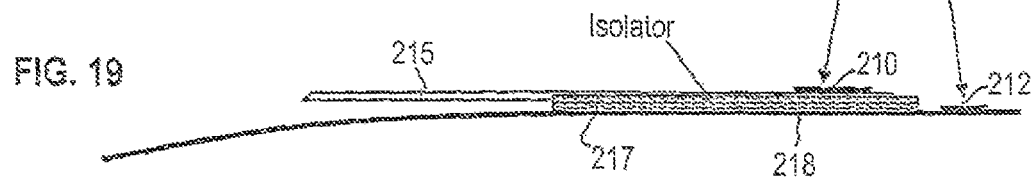
FIG. 20 illustrates yet another embodiment of a flexible structure used as a contact detector in which detection of the deflection of the flexible structure at the edges of an alignment mark is effected by measuring the voltage induced in one coil formed on the flexible structure by a second coil formed thereon.
Figure 20:
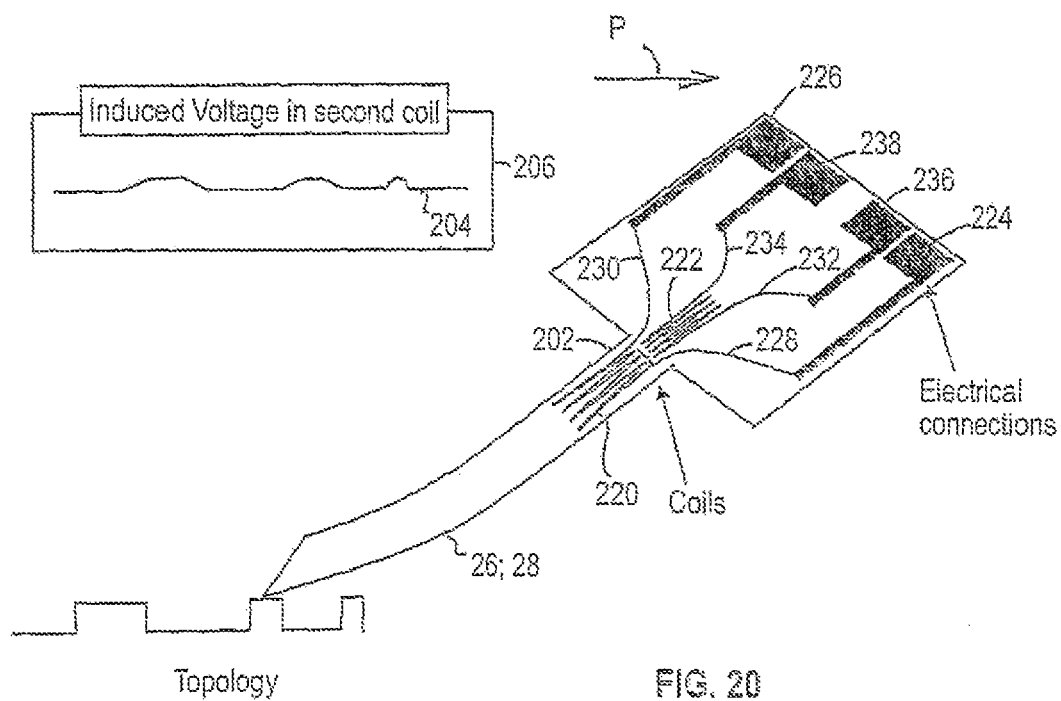

In FIG. 20 two coils 220 and 222 are realised on the flexible structure one at its base 202 and the other 222 on the wafer in close proximity to the first coil 220. A voltage applied to the first coil 220 via its respective electrodes 224 and 226 and leads 228 and 230 induces a changing voltage in the second coil due to the relative movement with changing bending deflection of the flexible structure and results in the induced voltage signal 204 in the inset 206 as the flexible structure 26 or 28 is moved relative to the edges of the alignment mark 22 or 24 in the direction of the arrow P. This induced voltage is picked up via the leads 232 and 234 at the electrodes 236 and 238 on the wafer forming the template.

Figure 21:
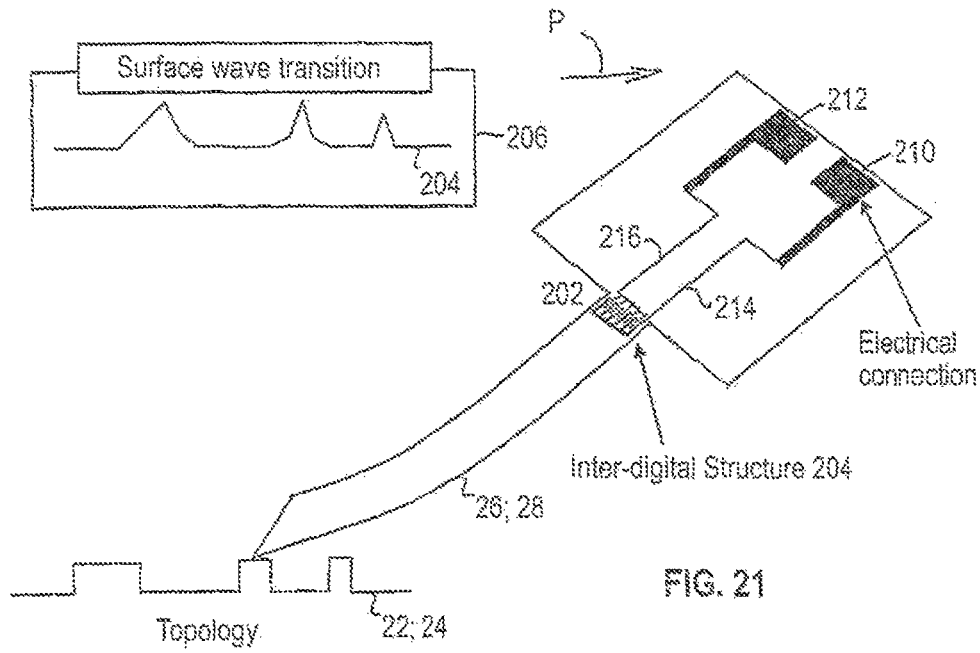
FIG. 21 illustrates one embodiment of a flexible structure used as a contact detector in which detection of the deflection of the flexible structure at the edges of an alignment mark is effected by a surface wave transition at an interdigital structure formed on the flexible structure.

In FIG. 21 an interdigital structure 240 similar to a SAW device is present on the flexible structure in the vicinity of its base 202 and bending deflections of the flexible structure 26 or 28 as it is moved in the direction of the arrow P with changing deflection at the edges of the alignment mark results in a surface wave transition signal which can be picked up at the electrical contacts 210 and 212 via the leads 214 and 216. again the shape of the surface wave transition signal provides information on the positions of the edges of the alignment mark 22 or 24.

A discussion of various known methods for forming semiconductor circuits using printing techniques and of various other concepts useful for an understanding of the invention will now be given in the following appendix. It will be appreciated that the present invention can be used in conjunction with all these methods to achieve high alignment accuracy.

APPENDIX AND DISCUSSION OF STATE OF THE ART PRACTICES

The technology is typically referred to as Step and Flash Imprint Lithography (S-FIL). For the further development of nanoimprint lithography the related overlay problems must be solved if this type of technology is to be applied to high-density silicon integrated circuitry. Nanoimprint lithography is generally understood to cover a class of new methods for the replication of nanometer-scale patterns down to 10 nm on solid materials.

Three different varieties of nanoimprint lithography will now be discussed. Soft lithography generally refers to the process of transferring a self-assembled monolayer using a flexible template as described in the paper by Whitesides et al. Y. Xia and G. M. Whitesides, Angew. Chem., Int. Ed. Engl. 37, 550 (1998). These authors formed a template by applying a liquid precursor to polydimethylsiloxane over a master mask produced using either electron beam or optical lithography.

A second process known as first nanoimprint lithography (NIL), developed by Chou et al is described in the paper by S. Y. Chou, P. R. Krauss, and P. J. Renstrom, J. Vac. Sci. Technol. B 14, 4129 (1996). These authors use a solid mold, such as silicon or nickel. The imprint process is accomplished by heating a resist above its glass transition temperature and imparting a relatively large force to transfer the image into the heated resist.

A derivative of NIL, ultraviolet nanoimprint lithography (or UV-NIL) addresses the issue of alignment by using a transparent template, thereby facilitating conventional optically aligned overlay techniques. The use of a quartz template enables the photocuring process to occur and also opened up the potential for optical alignment of the wafer and the template. In addition, the imprint process is performed at low pressures and at room temperature, which minimizes magnification and distortion errors. In this connection reference is made to the papers by M. Otto, M. Bender, B. Hadam, B. Spangenberg, and H. Kurz, Microelectron. Eng. 57, 361 (2001) and M. Colburn, S. Johnson, M. Stewart, S. Damle, T. Bailey, B. Choi, M. Wedlake, T. Michaelson, S. V. Sreenivasan, J. Ekerdt, and C. G. Willson, Proc. SPIE 379 (1999).

It is important to note that nanoimprint lithography is still at the start of its development, there are several companies that are now offering cosmetic imprint tools. In addition to Molecular Imprints Inc. (USA), Electronic Visions Group (Austria), Nanonex (U.S.), Obducat (Sweden), and Suss Microtec (Germany) have systems ready for purchase.

The Step and Flash Imprint Lithography (S-FIL™) technology referred to above was developed at the University of Texas at Austin. The technique is based on the ancient craft of embossing, with an adaptation to modern semiconductor needs. The technique uses a fused silica template with a circuit pattern etched into it. A commercialized version of an S-FIL tool is now available from Molecular Imprints Inc.

The fused silica surface, covered with a release layer, is gently pressed into a thin layer of low viscosity, silicon-containing monomer. When illuminated by a UV lamp, the surface is polymerized into a hard material. Upon separation of the fused silica template, the circuit pattern is left on the surface. A residual layer of polymer between features is eliminated by an etch process, and a perfect replica of the pattern is ready to be used in semiconductor processing for etch or deposition. Only the template fabrication process, typically accomplished with an e-beam writer, limits the resolution of the features. Features as small as 20 nm have been made to date that exceed the present requirements of the ITRS (International Technology Roadmap Semiconductors).

S-FIL has several important advantages over conventional optical lithography and EUV lithography. The parameters in the classic photolithography resolution formula (kl, NA, and lambda) are not relevant to S-FIL because the technology does not use reduction lenses. Investigations, by Molecular Imprints Inc. and others, in the sub-100 nm regime indicate that the resolution is only limited by the pattern resolution on the template. The resolution of S-FIL is a direct function of the resolution of the template fabricating process. Therefore, the S-FIL tools are multi-generational and should have a longer life as compared to optical lithography tools that have to be replaced when the exposure wavelength is decreased (decreasing the wavelength increases the optical resolution, i.e. reduces the size of features which can be realised). S-FIL templates are typically fabricated using conventional optical phase-shift mask technology. Electron beam writers that provide high resolution (below 10 nm), but lack the throughput required for mass production, are used. S-FIL lithography therefore takes advantage of resolution offered by e-beam technology without compromising throughput and tool life.

S-FIL™ is a bi-layer approach using a low viscosity, UV-curable imprint solution deposited on an underlying organic planarization layer. The template is rigid and transparent, allowing for UV curing of the imprint solution.

With S-FIL, an organic planarization layer is spin-coated on a silicon substrate. Then a low viscosity, photopolymerizable imprint solution is dispensed in droplets on the wafer to form an etch barrier in the imprint area. The template is then lowered into liquid-contact with the substrate, displacing the solution, filling the imprint field, and trapping the photopolymerizable imprint solution in the template relief. Irradiation with UV light through the back side of the template cures the solution. The template separates from the substrate, leaving an organo-silicon relief image that is an exact replica of the template pattern. A short halogen etch is used to clear undisplaced, cured imprint solution. A subsequent oxygen reactive ion etch into the planarization layer amplifies the aspect ratio of the imprinted image.

The S-FIL™ template and substrate, which are typically less than 250 nanometers apart, are in liquid contact due to the low viscosity imprint solution, which also behaves as a lubricant. This facilitates fine adjustment of the wafer and template. Although workers in this field are confident that they can demonstrate alignment capabilities that rival conventional state of the art lithography systems what this means is optical alignment within about 100 nm.

Molecular Imprints Inc. describes imprint lithography as a 1x-pattern transfer process. The design and production of a high-quality template is therefore a key factor for its success. Currently, templates are prepared following standard phase-shift mask manufacturing techniques: A resist-on-chromium-coated quartz mask blank is patterned with an electron beam, and the exposed resist is developed away (i.e., a positive tone process). Then, the exposed chromium is removed with a dry etch process and the quartz is etched using a standard phase-shift etch process, creating topography in mask quartz.

The S-FIL™ technique from Molecular Imprints Inc. uses a standard 6-inch×6-inch×0.250-inch fused silica blank. During photomask processing the chrome is removed leaving only the circuit pattern etched into it. The photomask is divided into four quadrants and the pattern is generated (can be one or more layers). The scheme enables die to die inspection, improving ease of manufacturing. The final template is typically sized to a 65×65 mm size. This process is described in the following papers and articles:

"High resolution templates for step and flash imprint lithography" D. J. Resnick JM3 1(3) 284-289 (October 2002) and "Analysis of critical dimension uniformity for step and flash imprint lithography" David P. Mancini, Physical Sciences Research Laboratories, Motorola Labs, Tempe, Ariz. USA 85284

The invention claimed is:

1. A method of aligning a first article relative to a second article, the method comprising steps of:

providing said second article with at least one flexible structure fixed relative to said second article at at least one point, said flexible structure having a sensing tip and a thermal actuator permitting deflection of the flexible structure between at least a first advanced position and a second retracted position, the thermal actuator operates via differential thermal expansion;

providing said first article having at least one surface relief marking on said first article, the surface relief marking having a topology, providing a memory containing reference information which is pre-stored in said memory prior to initiation of aligning said first article relative to said second article, said reference information relating to the topology of said surface relief marking and during and after aligning said first article relative to said second article, deflecting said flexible structure to move the sensing tip to at least said first advanced position in which the sensing tip is disposed in front of a front face of said second article, providing a piezoresistive detector for measuring an interaction of the flexible structure with the surface relief marking and generating detector signals relating to said interaction, wherein the piezoresistive detector comprises four piezoresistors associated with the flexible structure;

identifying with the help of the detector signals, a relative position of the flexible structure and thus of the second article with respect to the surface relief marking by comparison of said detector signals relating to said interaction with the reference information pre-stored in said memory relating to the topology of said surface relief marking to generate position control signals relating to a desired alignment, generating relative movement between the first and second articles to achieve the desired alignment between the first and second articles defined by the surface relief marking, moving said sensing tip to said second retracted position, and generating relative contacting movement between said first and second articles in a position of the desired alignment with said sensor tip in said second retracted position.

2. The method in accordance with claim 1, including a step of providing a plurality of surface relief markings on said first article.

3. The method in accordance with claim 2, including steps of providing a plurality of flexible structures on said second article and providing a same number of flexible structures as there are surface relief markings.

4. The method in accordance with claim 1, wherein the flexible structure is selected from the group consisting of: a cantilever, a flexible bridge supported at first and second points, and a flexible membrane supported at a plurality of points.

5. The method in accordance with claim 1, wherein said detector generates a signal corresponding to edges of the surface relief marking and a relative position of the first and second articles is determined from said signal.

6. The method in accordance with claim 1, wherein the step of providing said first article having the at least one surface relief marking on said first article comprises the step of forming said at least one surface relief marking by integrally forming the at least one surface relief marking with said first article.

7. The method in accordance with claim 1, wherein said surface relief marking is selected from the group consisting of: a natural feature of said first article, and an artificial feature of said first article.

8. The method in accordance with claim 1, and further comprising forming said flexible structure integrally with said second article.

9. The method in accordance with claim 1, wherein said flexible structure is made separately from said second article and is subsequently physically connected to said second article.

10. The method in accordance with claim 1, wherein said first article is selected from the group consisting of: a conductive substrate, a semiconductor wafer, an insulating substrate, a glass, metal or plastic article, a biological sample or reagent carrier, and a chemical sample or reagent carrier.

11. The method in accordance with claim 1, wherein said second article is selected from the group consisting of: a template for nanoimprint photography, a biological reagent or sample carrier, a chemical reagent or sample carrier, a biological sample readout device, and a chemical sample readout device.

12. The method in accordance with claim 1, wherein said method of aligning said first article relative to said second article is repeated using a third article, or further articles, provided with another flexible structure cooperating with said surface relief marking provided on said first article.

* * * * *